(12) United States Patent
Chau et al.

(10) Patent No.: US 12,029,753 B2
(45) Date of Patent: ***Jul. 9, 2024

(54) BIOCOMPATIBLE MATERIAL AND METHODS FOR MAKING AND USING THEREOF

(71) Applicant: THE HONG KONG UNIVERSITY OF SCIENCE AND TECHNOLOGY, Kowloon (HK)

(72) Inventors: Ying Chau, Kowloon (HK); Yu Yu, Kowloon (HK)

(73) Assignee: THE HONG KONG UNIVERSITY OF SCIENCE AND TECHNOLOGY, Kowloon (HK)

(*) Notice: Subject to any disclaimer, the term of this patent is extended or adjusted under 35 U.S.C. 154(b) by 528 days.

This patent is subject to a terminal disclaimer.

(21) Appl. No.: 16/648,105

(22) PCT Filed: Sep. 18, 2018

(86) PCT No.: PCT/CN2018/106278
§ 371 (c)(1),
(2) Date: Mar. 17, 2020

(87) PCT Pub. No.: WO2019/057035
PCT Pub. Date: Mar. 28, 2019

(65) Prior Publication Data
US 2020/0254004 A1    Aug. 13, 2020

Related U.S. Application Data

(60) Provisional application No. 62/560,387, filed on Sep. 19, 2017.

(51) Int. Cl.
*A61K 31/728* (2006.01)
*A61K 9/06* (2006.01)
(Continued)

(52) U.S. Cl.
CPC ............ *A61K 31/728* (2013.01); *A61K 47/36* (2013.01); *A61K 9/06* (2013.01)

(58) Field of Classification Search
None
See application file for complete search history.

(56) References Cited

U.S. PATENT DOCUMENTS

2013/0079421 A1    3/2013  Aviv
2014/0328926 A1*  11/2014  Gravett ..................... A61P 9/00
                                                                  514/180

(Continued)

FOREIGN PATENT DOCUMENTS

CN         1694903 A      11/2005
CN       101045032 A      10/2007

(Continued)

OTHER PUBLICATIONS

PCT/CN2018/106278 International Search Report dated Dec. 20, 2018.

(Continued)

*Primary Examiner* — Kyung S Chang
(74) *Attorney, Agent, or Firm* — Honigman LLP; Thomas A. Wootton, Esq.; Jonathan P. O'Brien

(57) ABSTRACT

The present disclosure provides compositions comprising one or more polymers capable of forming a hydrogel and methods for making and using the same. More specifically, the present disclosure provides compositions comprising one or more polymers capable of forming a hydrogel with prolonged mucosal retention, and methods for making and using the same.

9 Claims, 5 Drawing Sheets

(51) Int. Cl.
*A61K 47/36* (2006.01)
*C08J 3/075* (2006.01)

(56) References Cited

U.S. PATENT DOCUMENTS

2015/0352142 A1    12/2015   Gravett et al.
2019/0262259 A1*   8/2019    Yoneto ................ A61K 9/0056

FOREIGN PATENT DOCUMENTS

| CN | 102573941 A | 7/2012 |
| CN | 103038699 A | 4/2013 |
| CN | 103732264 A | 4/2014 |
| CN | 105026480 A | 11/2015 |
| WO | 2010054829 A1 | 5/2010 |
| WO | 2012145439 A1 | 10/2012 |
| WO | 2014174450 A1 | 10/2014 |
| WO | 2015078713 A1 | 6/2015 |
| WO | 2017162676 A1 | 9/2017 |

OTHER PUBLICATIONS

Nwokocha, Louis M., Solution characteristics and thermorheology of Prosopis africana seed polysaccharide, Food Hydrocolloids, vol. 56, pp. 201-206, 2016, Elsevier Ltd.

Xiao, Qian, et al., Pullulan-sodium alginate based edible films: Rheological properties of film forming solutions, Carbohydrate Polymers, vol. 87, pp. 1689-1695, 2012, Elsevier Ltd.

Xu, Xiaojuan, et al., Rhelogical behavior of Aeromonas gum in aqueous solutions, Food Hydrocolloids, vol. 20, pp. 723-729, 2006, Elsevier Ltd.

* cited by examiner

BIOCOMPATIBLE MATERIAL AND METHODS FOR MAKING AND USING THEREOF

CROSS-REFERENCE TO RELATED APPLICATIONS

This application is a National Stage Application and claims priority under 35 U.S.C. § 371 to Patent Cooperation Treaty application PCT/CN2018/106278, filed Sep. 18, 2018, which claims the benefit of U.S. Provisional Application 62/560,387, filed Sep. 19, 2017, priority is claimed to these applications and the disclosures of these prior applications are considered part of the disclosure of this application and to the extent allowed the entire contents of the aforementioned applications are incorporated herein.

BACKGROUND OF THE INVENTION

Many polymers used in biomedical applications are hydroxyl-bearing water soluble polymers. Examples of hydroxyl-bearing water soluble polymers include: hyaluronic acid (HA), polyethylene glycol (PEG), polyvinyl alcohol, alginate, cyclodextrin, and the like. Hydroxyl-bearing water soluble polymers are generally non-toxic, and the hydroxyl groups generally allow these polymers to be soluble in an aqueous environment. However, hydroxyl-bearing water soluble polymers alone do not usually have functionality toward animal cells or tissues and must be modified to exhibit desired properties.

For example, hydroxyl-bearing water soluble polymer can be modified for use as a hydrogel. Modifying hydroxyl-bearing water soluble polymers for use in a hydrogel traditionally involves complicated chemistry and harsh conditions, which may be expensive and not suitable for biomedical applications.

Thus, there is a need to generate hydrogels having desired properties with properly modified hydroxyl-bearing polymers.

SUMMARY OF THE INVENTION

The present disclosure provides compositions comprising a polymer (e.g., a biocompatible polymer) capable of forming a hydrogel and methods for making and using the same. For example, the composition may comprise one or more hydrogel forming polymers having an intrinsic viscosity [η] of at least 3 dL/g in the composition (e.g., as measured by a Ubbelohde viscometer). A concentration $C_T$ of the hydrogel forming polymers in the composition may be at most about 5 mg/ml. More specifically, the present disclosure provides compositions comprising a polymer (e.g., a biocompatible polymer) capable of forming a soft hydrogel, and methods for making and using the same. The hydrogels formed according to the present disclosure may have a relatively low G' (e.g. with a G' less than about 10.0 Pa), a higher G' comparing to G" (e.g G"/G'<1) while having relatively large yield strain (e.g., ≥10%). Accordingly, the hydrogels formed according to the present disclosure are suitable for being spread on surfaces. In addition, the hydrogels formed according to the present disclosure may be self-healing. The hydrogel of the present disclosure may have a low viscosity (e.g., with a complex viscosity of no more than about 0.2 Pa·s) at high shear rate, indicating that it might be easy to spread across a surface with the help of only a small force. In addition, viscosity of the hydrogel according to the present disclosure may increase exponentially towards low shear rate, indicating that it may be stable at rest. Moreover, the hydrogel of the present disclosure may be able to move freely in water without dissolution and could still show this property even after prolonged (e.g., for 24 hours or longer) period of time of being soaked in water.

In one aspect, the present disclosure provides a composition comprising a polymer capable of forming a hydrogel, wherein the polymer has a concentration C of about 0.1 mg/ml to about 5 mg/ml (e.g., about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

In another aspect, the present disclosure provides a composition comprising one or more hydrogel forming polymers having an intrinsic viscosity [η] of at least 3 dL/g (e.g., at least 5 dL/g, at least 8 dL/g, at least 10 dL/g, at least 12 dL/g, at least 15 dL/g, at least 16 dL/g, at least 17 dL/g, at least 18 dL/g, at least 19 dL/g, at least 20 dL/g, at least 25 dL/g, or more) in the composition, wherein a concentration $C_T$ of such hydrogel forming polymer in the composition is at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). The intrinsic viscosity [η] may be as measured by a Ubbelohde viscometer.

In another aspect, the present disclosure provides a composition comprising one or more polymers capable of forming a hydrogel, wherein a concentration C (e.g., total concentration) of the one or more polymers (e.g., hydrogel forming polymers) in the composition is at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less); and wherein at least one of the one or more polymers has an intrinsic viscosity [η] of at least about 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition.

In some embodiments, each of the one or more polymers has an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition.

In some embodiments, for a polymer in the composition, its concentration C is about 0.8 to about 5 times (e.g., about 0.8 to about 4.5 times, about 0.8 to about 4.0 times, about 0.8 to about 3.5 times, about 0.8 to about 3.0 times, about 0.8 to about 2.5 times, about 0.8 to about 2.0 times, about 0.8 to about 1.5 times, about 1.0 to about 1.2 times, about 1.8 to about 2.0 times, or about 1.0 to about 2.0 times) of a concentration C*, and wherein the C*=1/([η]), and said [η] is the intrinsic viscosity of the polymer.

In some embodiments, the polymer in the composition has a [η] that is at least 3 dL/g (e.g., at least 5 dL/g, at least 8 dL/g, at least 10 dL/g, at least 12 dL/g, at least 15 dL/g, at least 16 dL/g, at least 17 dL/g, at least 18 dL/g, at least 19 dL/g, at least 20 dL/g, at least 25 dL/g, or more).

In some embodiments, at least some of the hydrogel forming polymers are comprised in the composition in a hydrogel formed.

The hydrogel may have at least one of the followings:
1) a storage modulus G' of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test;
2) a loss modulus G" of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test;
3) a complex viscosity of no more than about 0.2 Pa·s (e.g., no more than about 0.1 Pa·s, no more than about 0.08 Pa·s, no more than about 0.07 Pa·s, no more than about 0.06 Pa·s, no more than about 0.05 Pa·s, or no more than about 0.04 Pa·s) as measured in a dynamic oscillatory shear test at a frequency of less than about 100 rad/s (e.g., less than about 90 rad/s, less than about 80 rad/s, less than about 70 rad/s, less than about 50 rad/s, less than about 40 rad/s, less than about 30 rad/s, less than about 20 rad/s, less than about 10 rad/s or less);
4) a yield strain of at least about 10% (e.g. at least about 10%, 9%, 8%, 7%, 6%, 5%, 4%, 3%, 2%, 1%, 0.5%, 0.2%, or 0.1%), as measured in a dynamic oscillatory strain sweep test.

In some embodiments, the hydrogel has a loss modulus G" that is no more than about 100% of its storage modulus G', as measured in a dynamic oscillatory shear test.

In some embodiment, the polymer is hydrophilic and/or water soluble.

In some embodiment, the polymer is selected from the group consisting of a polysaccharide, a poly (acrylic acid), a poly(hydroxyethylmethacrylate), an elastin, a collagen, a derivative thereof, and any combinations thereof. For example, the polymer is selected from the group consisting of a poly (acrylic acid), a poly(hydroxyethylmethacrylate), a derivative thereof, and any combinations thereof.

In some embodiments, the polymer is selected from the group consisting of a hyaluronic acid, a guar gum, a starch, a chitosan, a chondroitin sulfate, an alginate, a carboxymethylcellulose, a derivative thereof, and any combinations thereof. For example, the polymer is selected from the group consisting of a hyaluronic acid, a guar gum, an alginate, a carboxymethylcellulose, a derivative thereof, and any combinations thereof.

In some embodiments, the polymer is selected from the group consisting of a hyaluronic acid, a derivative thereof, and any combinations thereof.

In some embodiments, the polymer is modified with one or more modifications (e.g., a polymer derivative) selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof. For example, the polymer is modified with one or more modifications selected from the group consisting of a maleimide, a vinylsulfone, a N-hydroxysuccinimide, an aldehyde, a mercaptonicotinamide, a quinone, a thiol, an amine, and any combinations thereof.

For example, the polymer may comprise a derivative modified with one or more modifications selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof. For example, the polymer may comprise a derivative modified with one or more modifications selected from the group consisting of a maleimide, a vinylsulfone, a N-hydroxysuccinimide, an aldehyde, a mercaptonicotinamide, a quinone, a thiol, an amine, and any combinations thereof.

The derivative may have an average degree of modification (DM) of about 3% to about 50% (e.g., about 4% to about 45%, about 5% to about 40%, about 6% to about 40%, about 7% to about 40%, about 8% to about 39%, about 8% to about 38%, about 8% to about 35%, about 9% to about 32%, about 8% to about 30%, about 10% to about 30%, about 12% to about 30%, about 13% to about 30%, about 14% to about 30%, about 15% to about 35%, or about 15% to about 30%).

In some embodiments, the polymer comprises at least a first polymer population comprising the polymer modified with a first modification and a second polymer population comprising the polymer modified with a second modification, wherein the first modification is different from the second modification, and wherein polymers of the first polymer population react with polymers of the second polymer population to form the hydrogel. In some embodiments, a ratio between the polymers comprised in the first polymer population and the polymers comprised in the second polymer population is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10). In some embodiments, a ratio between the polymers comprised in the first polymer population and the polymers comprised in the second polymer population is from about 3:1 to about 1:3. For example, a ratio between the polymers comprised in the first polymer population and the polymers comprised in the second polymer population may be from about 2:1 to about 1:2.

The ratio may be a mass ratio, a molar ratio, a volume ration, and/or a DM ratio. For example, the ratio may be from about 3:1 to about 1:3, or from about 2:1 to about 1:2, such as about 1:1. A DM ratio refers to a ratio between an average DM of polymers of the first polymer population to an average DM of polymers if the second polymer population.

In some embodiments, the composition comprises at least a first polymer derivative and a second polymer derivative, wherein the first polymer derivative comprises a first modification and the second polymer derivative comprises a second modification, the first modification is different from the second modification, and the first polymer derivative is capable of reacting with the second polymer derivative to form the hydrogel.

A mass ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

A molar ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

A volume ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

In some embodiments, the first polymer derivative has a first DM (DM1), the second polymer derivative has a second DM (DM2), and a ratio between the first DM (DM1) and the second DM (DM2) is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

In some embodiments, the first modification and the second modification are independently selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof.

In some embodiments, the first modification and the second modification are independently selected from the group consisting of a maleimide, a vinylsulfone, a N-hydroxysuccinimide, an aldehyde, a mercaptonicotinamide, a quinone, a thiol, an amine, and any combinations thereof.

In some embodiments, the polymer is a hyaluronic acid, the first polymer population comprises hyaluronic acids modified with one or more vinylsulfone groups, the second polymer population comprises hyaluronic acids modified with one or more thiol groups, and wherein polymers of the first polymer population are able to react with polymers of the second polymer population to form the hydrogel.

For example, the one or more polymers may be hyaluronic acid derivatives, the first polymer derivative may be a hyaluronic acid modified with one or more vinylsulfone groups, the second polymer derivative may be a hyaluronic acid modified with one or more thiol groups, and wherein the first polymer derivative is capable of reacting with the second polymer derivative to form the hydrogel.

In some embodiments, the polymer has an average molecular weight from about 100,000 to about 5,000,000 dalton (e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton).

In some embodiments, the polymer comprises polymers with modifications (polymer derivatives), which may have an average degree of modification of about 3% to about 50% (about 4% to about 45%, about 5% to about 40%, about 6% to about 40%, about 7% to about 40%, about 8% to about 39%, about 8% to about 38%, about 8% to about 35%, about 9% to about 32%, about 8% to about 30%, about 10% to about 30%, about 12% to about 30%, about 13% to about 30%, about 14% to about 30%, about 15% to about 35%, or about 15% to about 30%).

In some embodiments, the composition further comprises a crosslinker (e.g., a crosslinker different from the polymers in the composition). The crosslinker may be a small molecule crosslinker, a macromolecule crosslinker, or any combination thereof.

For example, the crosslinker may be a small molecule crosslinker comprising a molecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

In some embodiments, the crosslinker is a macromolecule crosslinker comprising a macromolecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and combinations thereof.

In some embodiments, the crosslinker is selected from the group consisting of dithiothreitol, di-cysteine, PEG-dithiol, 4 or 8 arm-PEG thiol, divinyl sulfone, Bis(vinylsulfonyl)methane, PEG-VS and 4 or 8 arm-PEGVS.

In some embodiments, the polymer is modified with one or more vinylsulfone groups and the crosslinker is a thiol containing molecule. For example, the crosslinker may be selected from the group consisting of dithiothreitol, di-cysteine, PEG-dithiol, and 4 or 8 arm-PEG thiol.

In some embodiments, the polymer is modified with one or more thiol groups and the crosslinker is a vinylsulfone containing molecule. For example, the crosslinker is selected from the group consisting of divinyl sulfone, Bis(vinylsulfonyl)methane, PEG-VS and 4 or 8 arm-PEGVS.

In some embodiments, the composition does not comprise any crosslinker different from the polymer in the composition. For example, the composition does not comprise a small molecule crosslinker or a PEG based crosslinker.

In some embodiments, besides the polymers of the present disclosure, the composition does not comprise any additional crosslinker.

In some embodiments, the composition comprises a buffer. The buffer may be a phosphate buffer.

In some embodiments, the composition has a pH of about 3.5 to about 9.0 (e.g., about 4.0 to about 9.0, about 4.5 to about 9.0, about 5.0 to about 9.0, about 5.5 to about 9.0, about 6.0 to about 9.0, about 6.5 to about 9.0, about 7.0 to about 9.0, about 7.5 to about 9.0, about 8.0 to about 9.0, about 8.5 to about 9.0, about 7.0 to about 7.8, or about 7.4).

In another aspect, the present disclosure relates to a hydrogel formed by the composition of the present disclosure.

In some embodiments, the hydrogel is biocompatible.

In some embodiments, the hydrogel has a storage modulus G' of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test.

In some embodiments, the hydrogel has a loss modulus G" that is no more than about 100% (e.g., no more than about 90%, no more than about 80%, no more than about 70%, no more than about 60%, no more than about 55%, no more than about 50%, no more than about 45%, no more than about 40%, no more than about 35%, no more than about 30%, no more than about 25%, or no more than about 20%) of its storage modulus G' as measured in a dynamic oscillatory shear test.

In some embodiments, the hydrogel has a complex viscosity that is no more than about 0.2 Pa·s (e.g., no more than about 0.1 Pa·s, no more than about 0.08 Pa·s, no more than about 0.07 Pa·s, no more than about 0.06 Pa·s, no more than about 0.05 Pa·s, or no more than about 0.04 Pa·s) as measured in a dynamic oscillatory shear test at a frequency of more than about 100 rad/s.

In some embodiments, the hydrogel has a yield strain of at least about 10% (e.g., at least about 20%, at least about 30%, at least about 40%, at least about 50%, at least about 60%, at least about 70%, at least about 80%, at least about 90%, at least about 95%, at least about 100%, at least about 110%, or higher), as measured in a dynamic oscillatory strain sweep test.

In another aspect, the present disclosure relates to a method for generating a hydrogel (such as a hydrogel of the present disclosure). The method may comprise: a) providing a composition of the present disclosure; and subjecting the composition to conditions enabling formation of the hydrogel.

In some embodiments, the subjecting comprises incubating the composition at about 30° C. to about 45° C. (e.g., at about 32° C. to about 40° C., at about 35° C. to about 40° C., such as at about 37° C.).

In some embodiments, the method may comprise: 1) preparing a first polymer population and a second polymer population (e.g., polymers in the first polymer population may comprise hyaluronic acids modified with one or more vinylsulfone groups, with a molecular weight of about 2,600,000 dalton, and a degree of modification of about 30%; and polymers in the second polymer population may comprise hyaluronic acids modified with one or more thiol groups, with a molecular weight of about 2,600,000 dalton, and a degree of modification of about 30%) in water, adjusting the pH to be about 7.4 (for example, by adding a buffer solution); 2) mixing polymers of the first polymer population with those of the second polymer population at a ratio (e.g., mass ratio) of about 1:1, the concentration C (e.g., total concentration) of the polymers is about 0.3-0.5 mg/ml; and 3) incubate the mixture at about 370 for about 24 hours.

In some embodiments, the method may comprise: 1) preparing a first polymer population and a second polymer population (e.g., polymers in the first polymer population may comprise hyaluronic acids modified with one or more vinylsulfone groups, with a molecular weight of about 2,600,000 dalton, and a degree of modification of about 8%; and polymers in the second polymer population may comprise hyaluronic acids modified with one or more thiol groups, with a molecular weight of about 2,600,000 dalton, and a degree of modification of about 8%) in water, adjusting the pH to be about 7.4 (for example, by adding a buffer solution); 2) mixing polymers of the first polymer population with those of the second polymer population at a ratio (e.g., mass ratio) of about 1:1, the concentration (e.g., total concentration) C of the polymers is about 0.3-0.5 mg/ml; and 3) incubate the mixture at about 37° C. for about 24 hours.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DE TAILED DESCRIPTION

Figure 1:
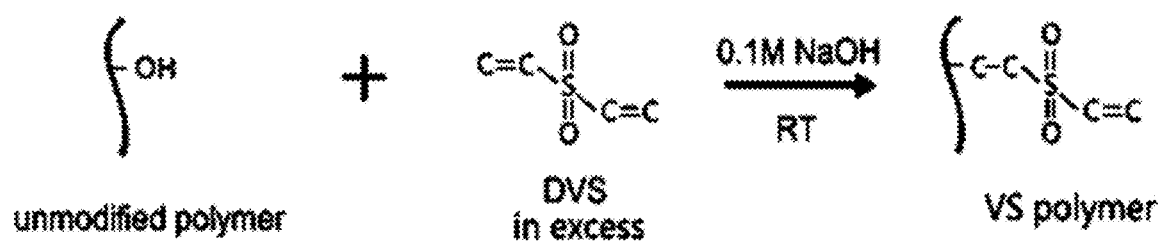
FIG. 1 illustrates the synthesis of HA-VS polymer.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "biocompatible" or "biocompatibility", as used herein, generally refers to a condition of being compatible with a living tissue or a living system by not being toxic, injurious, or physiologically reactive and/or not causing immunological rejection.

The term "polymer", as used herein, generally refers to a chemical compound or mixture of compounds formed by polymerization and consisting essentially of repeating structural units.

The term "hydrogel", as used herein, generally refers to a gel or gel-like structure comprising one or more polymers suspended in an aqueous solution (e.g., water).

The term "viscosity", as used herein, generally refers to a property of resistance to flow in a fluid or semifluid.

The term "intrinsic viscosity", as used herein, generally refers to a measure of a substance's (e.g., a polymer) contribution to the viscosity of a system (e.g., a solution). In the present disclosure, the intrinsic viscosity [η] may be measured by a Ubbelohde viscometer, or a differential viscometer. Alternatively, the intrinsic viscosity [η] may be calculated from Mark-Houwink equation from established relation between intrinsic viscosity and molecular weight.

The term "hydrogel forming polymer", as used herein, generally refers to a polymer participating in the formation of a hydrogel. It may be a naturally occurring polymer or a synthetic polymer capable of forming a hydrogel. The hydrogel forming polymer may include polymer(s) making a contribution to hydrogel formation. In some embodiments, the hydrogel forming polymer does not include polymers that are not able to participate in hydrogel formation, and/or polymers unable to form a hydrogel, even if present in the composition of the present disclosure. In some cases, the hydrogel forming polymer may also be referred to as "a backbone polymer".

The term "$C_T$", as used herein, generally refers to the total concentration of a polymer or polymers in a composition. For example, $C_T$ of the hydrogel forming polymer may refer to the total concentration of the polymers forming and/or formed the hydrogel of the present disclosure. For instance, it may refer to the total concentration of the hydrogel forming polymers present in the composition of the present disclosure. In some cases, the composition of the present disclosure may comprise hydrogel forming polymers that have already formed the hydrogel, and/or hydrogel forming polymers that have not yet been incorporated in a hydrogel, and $C_T$ of the hydrogel forming polymers may refer to the total concentration of the hydrogel forming polymers present in the composition (e.g., including both the polymers already incorporated in the hydrogel and those not yet incorporated). In another example, $C_T$ of the hydrogel forming polymers having an intrinsic viscosity [η] of at least 3 dL/g, may refer to the total concentration of the hydrogel forming polymers that have an intrinsic viscosity [η] of at least 3 dL/g.

The term "storage modulus", as used herein, generally represents the stored energy as measured, representing the elastic portion.

The term "substantial", as used herein, generally refers to more than a minimal or insignificant amount; and "substantially" generally refers to more than minimally or insignificantly. The term "a substantial part of", as used herein, generally refers to an amount, quantity, sequence, length, concentration etc. of a part of an object that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% of that of the entire amount, quantity, sequence, length, concentration etc. of the corresponding object.

The term "fluorescer" or "fluorescent moiety" as used herein, generally refers to a substance or a portion thereof which is capable of exhibiting fluorescence in the detectable range. Exemplary detectable moieties suitable for use as detectable labels may include e.g., affinity tags and fluorescent proteins.

The term "consists essentially of", as used herein, generally refers to a substantial part being made of the indicated components or ingredients.

The term "a loss modulus G"", as used herein, generally refers to the lost energy as measured, representing the viscous portion.

The term "yield strain", as used herein, generally refers to the strain at which a material begins to deform plastically whereas yield point is the point where nonlinear (elastic and plastic) deformation begins. Prior to the yield point, the material will deform elastically and will return to its original shape when the applied stress is removed.

The term "hydrophilic", as used herein, generally refers to having an affinity for water, able to absorb or be wetted by water. A hydrophilic molecule or portion of a molecule is one whose interactions with water and other polar substances are more thermodynamically favorable than their interactions with oil or other hydrophobic solvents.

The term "average degree of modification (DM)", as used herein, generally refers to the percentage of repeating units with pendant group in a polymer. DM may reflect the degrees of modification of hydrogel forming polymer derivative.

The term "cross-linker", as used herein, generally refers to an agent that links one polymer chain to another with bonds. The cross-linker can achieve crosslink through covalent bonds or noncovalent bonds. The "polymer chains" may refer to synthetic polymers or natural polymers (such as proteins). In polymer chemistry, when a synthetic polymer is the to be "cross-linked", it usually means that the entire bulk of the polymer has been exposed to the cross-linking method. The resulting modification of mechanical properties depends strongly on the cross-link density. Crosslinks may be formed by chemical reactions that are initiated by heat, pressure, change in pH, or radiation.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

The term "soft hydrogel", as used herein, generally refers to a hydrogel having a relatively low G' (e.g. <1 or about 1 Pa) and/or a higher G' comparing to G" (e.g G"/G'<1) while having relatively large yield strain (e.g. ≥10%, ≥20%, ≥50%, ≥70%, or even ≥100%). For example, the soft hydrogel may be especially suitable for being spread on surfaces.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

As will be understood by those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

The present disclosure provides compositions comprising a polymer capable of forming a hydrogel and methods for making and using the same. For example, the composition may comprise one or more hydrogel forming polymers having an intrinsic viscosity [η] of at least 3 dL/g in the composition (e.g., as measured by a Ubbelohde viscometer). A concentration $C_T$ of the hydrogel forming polymers in the composition may be at most about 5 mg/ml. More specifically, the present disclosure provides compositions comprising a polymer capable of forming a soft hydrogel, and methods for making and using the same.

In one aspect, the present disclosure provides a composition comprising a polymer capable of forming a hydrogel, such as a composition comprising one or more polymers capable of forming a hydrogel. The polymer, or the one or more polymers in the composition may have a concentration C of at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). For example, the polymer, or the one or more polymers in the composition may have a concentration C of about 0.05 mg/ml to about 5 mg/ml (e.g., about 0.1 mg/ml to about 5 mg/ml, about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

In another aspect, the present disclosure provides a composition comprising one or more hydrogel forming polymer(s). Such hydrogel forming polymers may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition. For example, as measured by a Ubbelohde viscometer. In some embodiments, the intrinsic viscosity [η] is measured by a differential viscometer. Alternatively, the intrinsic viscosity [η] may be calculated from Mark-Houwink equation from established relation between intrinsic viscosity and molecular weight.

The total concentration of the hydrogel forming polymer(s) (e.g., of those hydrogel forming polymers having an intrinsic viscosity [η] of at least 3 dL/g) in the composition is $C_T$. The $C_T$ may be at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). For example, the $C_T$ may be about 0.05 mg/ml to about 5 mg/ml (e.g., about 0.1 mg/ml to about 5 mg/ml, about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

In some cases, the polymer, the one or more polymers, or the hydrogel forming polymers in the composition may have a concentration C of about 0.01% w/v) to about 4% (w/v), e.g., about 0.02% (w/v) to about 4% (w/v), about 0.03% (w/v) to about 4% (w/v), about 0.04% (w/v) to about 4% (w/v), about 0.05% (w/v) to about 4% (w/v), about 0.06% (w/v) to about 4% (w/v), about 0.07% (w/v) to about 4% (w/v), about 0.08% (w/v) to about 4% (w/v), about 0.09% (w/v) to about 4% (w/v), about 0.1% (w/v) to about 4% (w/v), about 0.11% (w/v) to about 4% (w/v), about 0.12% (w/v) to about 4% (w/v), about 0.13% (w/v) to about 4% (w/v), about 0.14% (w/v) to about 4% (w/v), about 0.15% (w/v) to about 4% (w/v), about 0.2% (w/v) to about 4% (w/v), about 0.25% (w/v) to about 4% (w/v), about 0.3% (w/v) to about 4% (w/v), about 0.4% (w/v) to about 4% (w/v), about 0.5% (w/v) to about 4% (w/v), about 0.6% (w/v) to about 4% (w/v), about 0.7% (w/v) to about 4% (w/v), about 0.8% (w/v) to about 4% (w/v), about 0.9% (w/v) to about 4% (w/v), about 1% (w/v) to about 4% (w/v), about 2% (w/v) to about 4% (w/v), about 3% (w/v) to about 4% (w/v), or about 3.5% (w/v) to about 4% (w/v).

The polymer, at least one of the one or more polymers, or the hydrogel forming polymers may have an intrinsic viscosity [η] of at least about 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition.

In some cases, each of the one or more polymers, or the hydrogel forming polymers, may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition.

For example, when there is just one kind of polymer (e.g., hydrogel forming polymers) in the composition, this polymer may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition. When there are two or more kinds of polymers (e.g., hydrogel forming polymers) in the composition, one or more of them, or even each of them, may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition.

For a polymer (e.g., a hydrogel forming polymer) in the composition, its concentration C may be about 0.8 to about 5 times (e.g., about 0.8 to about 4.5 times, about 0.8-about 4.0 times, about 0.8-about 3.5 times, about 0.8-about 3.0 times, about 0.8-about 2.5 times, about 0.8-about 2.0 times, about 0.8 to about 1.5 times, or about 1.0 to about 1.2 times) of a concentration $C^*$, wherein $C^*=1/([\eta])$, and [η] is the intrinsic viscosity of the polymer.

For example, when there are two of more kinds of polymers (e.g., hydrogel forming polymers) in the composition, their total concentration in the composition may be $C_T$, while each kind of polymers may have a concentration C. The concentration C of one kind of polymer may be different from that of another kind of polymer. For each kind of polymer, its concentration C may be about 0.8 to about 5 times (e.g., about 0.8 to about 4.5 times, about 0.8-about 4.0 times, about 0.8-about 3.5 times, about 0.8-about 3.0 times, about 0.8-about 2.5 times, about 0.8-about 2.0 times, about 0.8 to about 1.5 times, or about 1.0 to about 1.2 times) of a concentration $C^*$, wherein $C^*=1/([\eta])$, and [η] is the intrinsic viscosity of the polymer.

In some cases, the total concentration $C_T$ of the hydrogel forming polymers (e.g., the hydrogel forming polymers having an intrinsic viscosity [η] of at least 3 dL/g in the composition) may be at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). For example, the total concentration $C_T$ of those hydrogel forming polymers having an intrinsic viscosity [η] of at least 3 dL/g may be about 0.05 mg/ml to about 5 mg/ml (e.g., about 0.1 mg/ml to about 5 mg/ml, about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

The composition may have a pH of about 3.5 to about 9.0, e.g., about 4.0 to about 9.0, about 4.5 to about 9.0, about 5.0 to about 9.0, about 5.5 to about 9.0, about 6.0 to about 9.0, about 6.5 to about 9.0, about 7.0 to about 9.0, about 7.5 to about 9.0, about 8.0 to about 9.0, about 8.5 to about 9.0, about 7.0 to about 7.8, or about 7.4.

In another aspect, the present disclosure provides a hydrogel formed by a composition of the present disclosure. The hydrogel may be biocompatible.

In some cases, initially, the hydrogel forming polymers in the composition may exist in non-crosslinked forms (e.g., the hydrogel has not been formed yet), and after certain treatment (e.g., after being incubated under for example, 37° C. for a certain period of time, e.g., 12 hours or longer), some of the hydrogel forming polymers may be chemically and/or physically crosslinked to form the hydrogel. In certain embodiments, almost all the hydrogel forming polymers are chemically and/or physically crosslinked to form the hydrogel.

Thus, in some cases, the composition may comprise hydrogels that have been formed. In such cases, at least some of the hydrogel forming polymers are comprised in the composition in the hydrogel formed. For example, the hydrogel forming polymers in the composition may comprise both polymers that have already formed the hydrogel, and polymers that have not yet been incorporated in a hydrogel but are capable of forming a hydrogel under certain reaction conditions (e.g., after being incubated under 37° C. for a period of time, e.g., 12 h). In such cases, the total concentration $C_T$ of both the hydrogel forming polymers already comprised in the hydrogel and those not yet incorporated in the hydrogel may be at most about 5 mg/ml.

In some cases, almost all the hydrogel forming polymers in the composition may have formed the hydrogel (e.g., through chemical and/or physical crosslinking).

The hydrogel according to the present disclosure may have one or more specific characteristics/properties.

For example, the hydrogel of the present disclosure may have a storage modulus G' of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test.

The hydrogel of the present disclosure may have a loss modulus G" that is no more than about 100% (e.g., no more than about 90%, no more than about 80%, no more than about 70%, no more than about 60%, no more than about 55%, no more than about 50%, no more than about 45%, no more than about 40%, no more than about 35%, no more than about 30%, no more than about 25%, or no more than about 20%) of its storage modulus G', as measured in a dynamic oscillatory shear test.

The hydrogel of the present disclosure may have a complex viscosity of no more than about 0.2 Pa·s (e.g., no more than about 0.1 Pa·s, no more than about 0.08 Pa·s, no more than about 0.07 Pa·s, no more than about 0.06 Pa·s, no more than about 0.05 Pa·s, or no more than about 0.04 Pa·s) as measured in a dynamic oscillatory shear test at a frequency of less than about 100 rad/s (e.g., less than about 90 rad/s, less than about 80 rad/s, less than about 70 rad/s, less than about 50 rad/s, less than about 40 rad/s, less than about 30 rad/s, less than about 20 rad/s, less than about 10 rad/s or less).

The hydrogel of the present disclosure may have a yield strain of at least about 10% (e.g., at least about 20%, at least about 30%, at least about 40%, at least about 50%, at least about 60%, at least about 70%, at least about 80%, at least about 90%, at least about 95%, at least about 100%, at least about 110%, or higher), as measured in a dynamic oscillatory strain sweep test.

For example, in the dynamic oscillatory shear test, a sinusoidal force (e.g., a stress) may be applied to a material and the resulting displacement (strain) may be measured. For a perfectly elastic solid, the resulting strain and the stress may be perfectly in phase. For a purely viscous fluid, there may be a 90 degree phase lag of strain with respect to stress. Viscoelastic polymers having characteristics in between may have a phase lag during the test, and the storage modulus may be calculated accordingly.

A dynamic mechanical analyzer (DMA) may be used to measure the storage modulus and may be used in a dynamic oscillatory shear test. In another example, a DMA analyzer may comprise a displacement sensor (such as a linear variable differential transformer), which may measure a change in voltage as a result of the instrument probe moving through a magnetic core. The DMA analyzer may further comprise a temperature control system or furnace, a drive motor (e.g., a linear motor for probe loading which may provide load for the applied force), a drive shaft support and a guidance system to act as a guide for the force from the motor to the sample, and one or more sample clamps in order to hold the sample being tested.

Different types of DMA analyzers may be used. For example, a forced resonance analyzer or a free resonance analyzer may be used. A free resonance analyzer may measure the free oscillations of damping of a sample being tested by suspending and swinging the sample. A forced resonance analyzer may force the sample to oscillate at a certain frequency and may be reliable for performing a temperature sweep. The analyzers may be made for both stress (force) and strain (displacement) control. For example, in strain control, the probe may be displaced and the resulting stress of the sample may be measured by implementing a force balance transducer, which may utilize different shafts. In stress control, a set force may be applied, and several other experimental conditions (temperature, frequency, or time) may be varied. The stress and strain may be applied via torsional or axial analyzers. With a torsional analyzer, the force is applied in a twisting motion. An axial analyzer may be used for flexure, tensile, and/or compression testing.

A variety of test modes may be employed to probe the viscoelastic properties of polymers, such as temperature sweep testing, frequency sweep testing, dynamic stress-strain testing, or a combination thereof. For example, in a dynamic stress-strain testing, by gradually increasing the amplitude of oscillations, a dynamic stress-strain measurement may be performed. The variation of storage and loss moduli with increasing stress may be used for material characterization, and to determine the upper bound of a material's linear stress-strain regime.

A variety of mechanical properties can be determined by DMA. These properties include storage modulus (G'), loss modulus (G"), complex modulus (G*), loss angle (tan (δ)), complex viscosity (η*), it's in phase (η') and out of phase component (η"), complex compliance (J*), storage compliance (J'), loss compliance (J") etc.

In another aspect, the present disclosure provides a method for generating a hydrogel (e.g., a hydrogel of the present disclosure). The method may comprise providing a composition (e.g., a composition comprising one or more polymers of the present disclosure); and subjecting the composition to conditions enabling formation of the hydrogel (e.g., enabling crosslinking of the polymer to form the hydrogel). For example, the conditions may comprise incubating the composition at about 30° C. to about 45° C., e.g., at about 32° C. to about 40° C., at about 35° C. to about 40° C., such as at about 37° C.).

The method may further comprise preparing a polymer as defined in the present disclosure in a buffer to form a polymer solution. The solution may comprise one or more kinds of polymers. The polymers (e.g., the hydrogel forming polymers) in the polymer solution may have a total concentration $C_T$ of at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less).

For example, the hydrogel forming polymers in the polymer solution may have a total concentration $C_T$ of about 0.1 mg/ml to about 5 mg/ml (e.g., about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

In some cases, the total concentration $C_T$ of the hydrogel forming polymers may be about 0.3-0.5 mg/ml, or less.

In some cases, the method may comprise cross-linking the polymers in the solution to generate the hydrogel. For example, the conditions enabling formation of the hydrogel may also enable cross-linking of the polymers in the solution.

The buffer may be an aqueous solution, and may comprise water and appropriate salts useful for adjusting the pH or buffering capacity of the aqueous solution. In some embodiments, the buffer comprises a phosphate buffer, such as Phosphate Buffered Saline (PBS).

Thus, the composition according to the present disclosure may further comprise a buffer, such as a phosphate buffer, e.g., a Phosphate Buffered Saline (PBS).

In a method of the present disclosure, the polymer solution may have a pH of about 3.5 to about 9.0, e.g., about 4.0 to about 9.0, about 4.5 to about 9.0, about 5.0 to about 9.0, about 5.5 to about 9.0, about 6.0 to about 9.0, about 6.5 to about 9.0, about 7.0 to about 9.0, about 7.5 to about 9.0, about 8.0 to about 9.0, about 8.5 to about 9.0, about 7.0 to about 7.8, or about 7.4.

In some cases, the polymer solution may have a pH of about 6 to 10, such as about 6.5 to 10, about 7 to 10, about 7.1 to 10, about 7.2 to 10, about 7.3 to 10, about 7.4 to 10, about 7.5 to 10, about 7.6 to 10, about 7.7 to 10, about 7.8 to 10, about 7.9 to 10, about 8.0 to 10, about 8.5 to 10, about 9 to 10, or about 9.5 to 10. In some embodiments, the polymer solution has a pH of about 7-8, such as about 7.4.

In a method of the present disclosure, the cross-linking may comprise incubating the polymer solution at about 20° C. to about 50° C., about 25° C. to about 50° C., about 30° C. to about 50° C., about 31° C. to about 50° C., about 32° C. to about 50° C., about 33° C. to about 50° C., about 34° C. to about 50° C., about 35° C. to about 50° C., about 36° C. to about 50° C., about 37° C. to about 50° C., about 38° C. to about 50° C., about 39° C. to about 50° C., about 40° C. to about 50° C., or about 45° C. to about 50° C. In some embodiments, the cross-linking comprises incubating the polymer solution at a temperature of about 30° C. to about 40° C., e.g., about 35° C. to about 39° C., such as at about 37° C.

In a method of the present disclosure, the cross-linking may comprise incubating the polymer solution for at least about 1 hour, e.g., for at least about 2 hours, for at least about 3 hours, for at least about 4 hours, for at least about 5 hours, for at least about 6 hours, for at least about 7 hours, for at least about 8 hours, for at least about 9 hours, for at least about 9.5 hours, for at least about 10 hours, for at least about 10.5 hours, for at least about 11 hours, for at least about 12 hours, for at least about 13 hours, for at least about 14 hours, for at least about 15 hours, for at least about 16 hours, for at least about 17 hours, for at least about 18 hours, for at least about 19 hours, for at least about 20 hours, for at least about 24 hours or more.

For example, in a method of the present disclosure, the cross-linking may comprise incubating the polymer solution at a temperature of about 30° C. to about 40° C. (e.g., about 35° C. to about 39° C., such as at about 37° C.) for at least 5 hours (e.g., for at least about 10 hours or longer, such as for about 24 hours or longer).

For example, the method may comprise: 1) preparing a first polymer population (or a first polymer derivative) and a second polymer population (or a second polymer derivative) (e.g., polymers in the first polymer population may comprise hyaluronic acids modified with one or more vinylsulfone groups; and polymers in the second polymer population may comprise hyaluronic acids modified with one or more thiol groups) in water, adjusting the pH (for example, by adding a buffer solution); 2) mixing polymers of the first polymer population (or the first polymer derivative) with those of the second polymer population (or the second polymer derivative) at a pre-set ratio, the concentration of the polymers in the composition is as defined in the present disclosure; and 3) incubate the mixture under conditions allowing formation of the hydrogel according to the present disclosure.

According to any aspect of the present disclosure, the polymer of the present disclosure may be hydrophilic and/or water soluble.

According to any aspect of the present disclosure, the polymer (e.g., the hydrogel forming polymers) may be selected from the group consisting of a polysaccharide, a poly (acrylic acid), a poly(hydroxyethylmethacrylate), an elastin, a collagen, a derivative thereof, and any combinations thereof. For example, the polymers (e.g., the hydrogel forming polymers) in the composition may comprise one or more of the following: a polysaccharide, one or more types of polysaccharide derivative, a poly (acrylic acid), one or more types of poly (acrylic acid) derivative, a poly (hydroxyethylmethacrylate), one or more types of poly (hydroxyethylmethacrylate) derivative, an elastin, one or more types of elastin derivative, a collagen and one or more types of collagen derivative.

For example, the polymer (e.g., the hydrogel forming polymers) may be selected from the group consisting of a hyaluronic acid, a guar gum, a starch, a chitosan, a chondroitin sulfate, an alginate, a carboxymethylcellulose, a derivative thereof, and any combinations thereof. For example, the polymers (e.g., the hydrogel forming polymers) in the composition may comprise one or more of the following: a hyaluronic acid, one or more types of hyaluronic acid derivative, a guar gum, one or more types of guar gum derivative, a starch, one or more types of starch derivative, a chitosan, one or more types of chitosan derivative, a chondroitin sulfate, one or more types of chondroitin sulfate derivative, an alginate, one or more types of alginate derivative, a carboxymethylcellulose and one or more types of carboxymethylcellulose derivative. In some embodiments, the polymers (e.g., the hydrogel forming polymers) in the composition comprise one or more of the following: a hyaluronic acid, and one or more types of hyaluronic acid derivative.

According to any aspect of the present disclosure, the polymer (e.g., the hydrogel forming polymers) may be modified with one or more modifications, e.g., to become a polymer derivative of the present disclosure. In one example, a polymer of the present disclosure (e.g., the hydrogel forming polymers) may be modified with one or more vinylsulfone groups (or with a molecule comprising one or more vinylsulfone groups). In another example, a polymer of the present disclosure (e.g., the hydrogel forming polymers) may be modified with one or more thiol groups (or with a molecule comprising one or more thiol groups).

For example, the polymer of the present disclosure may be modified with one or more modifications selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof.

For example, the polymer may comprise one or more polysaccharide derivative, which may be a polysaccharide modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more poly (acrylic acid) derivative, which may be a poly (acrylic acid) modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more poly (hydroxyethylmethacrylate) derivative, which may be a poly (hydroxyethylmethacrylate) modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more elastin derivative, which may be an elastin modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more collagen derivative, which may be a collagen modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine.

In one embodiment, the polymer comprises a derivative of hyaluronic acid modified with one or more thiol groups (HA-SH), in some cases, the HA-SHs may form HA-SH based polymer-polymer type hydrogel under proper conditions. In another embodiment, the polymer comprises a derivative of hyaluronic acid modified with one or more vinylsulfone groups (HA-VS), in some cases, the HA-VSs may form HA-VS based polymer-polymer type hydrogel under proper conditions. In another embodiment, the polymer comprises a derivative of hyaluronic acid modified with one or more thiol groups, as well as a derivative of hyaluronic acid modified with one or more vinylsulfone groups, in some cases, the HA-SH and the HA-VS may react with each other to form polymer-polymer type hydrogel under proper conditions.

The derivative may have an average degree of modification (DM) of about 3% to about 50% (e.g., about 4% to about 45%, about 5% to about 40%, about 6% to about 40%, about 7% to about 40%, about 8% to about 39%, about 8% to about 38%, about 8% to about 35%, about 9% to about 32%, about 8% to about 30%, about 10% to about 30%, about 12% to about 30%, about 13% to about 30%, about 14% to about 30%, about 15% to about 35%, or about 15% to about 30%).

According to any aspect of the present disclosure, the polymer (e.g., the hydrogel forming polymers) of the present disclosure may comprise at least a first polymer population comprising the polymer modified with a first modification and a second polymer population comprising the polymer modified with a second modification. The first modification may be different from the second modification. Polymers of the first polymer population may react with polymers of the second polymer population to form the hydrogel. A ratio (e.g., a mass ratio, a volume ratio, a molar ratio, and/or a DM ratio) between the polymers comprised in the first polymer population and the polymers comprised in the second polymer population may be from about 10:1 to about 1:10, e.g., from about 8:1 to about 1:10, from about 6:1 to about 1:10, from about 5:1 to about 1:10, from about 4:1 to about 1:10, from about 3:1 to about 1:10, from about 2:1 to about 1:10, from about 1.75:1 to about 1:10, from about 1.5:1 to about 1:10, from about 1.25:1 to about 1:10, from about 1:1 to about 1:10, from about 1:1.25 to about 1:10, from about 1:1.5 to about 1:10, from about 1:1.75 to about 1:10, from about 1:2 to about 1:10, from about 1:3 to about 1:10, from about 1:4 to about 1:10, from about 1:5 to about 1:10, from about 6:1 to about 1:6, from about 5:1 to about 1:5, from about 4:1 to about 1:4, from about 3:1 to about 1:3, from about 2:1 to about 1:2, from about 1.75:1 to about 1:1.75, from about 1.5:1 to about 1:1.5, from about 1.25:1 to about 1:1.25, or from about 1.1:1 to about 1:1.1.

For example, a ratio (e.g., a mass ratio, a volume ratio, a molar ratio, and/or a DM ratio) between the polymers comprised in the first polymer population and the polymers comprised in the second polymer population may be from about 3:1 to about 1:3. For example, the ratio may be from about 2:1 to about 1:2 (such as about 1:1).

For example, the composition may comprise at least a first polymer derivative and a second polymer derivative. The first polymer derivative may comprise a first modification and the second polymer derivative may comprise a second modification. The first modification may be different from the second modification. The first polymer derivative may be capable of reacting with the second polymer derivative to form the hydrogel. For example, the first polymer derivative may be a polymer (e.g., a hyaluronic acid) modified with one or more vinylsulfone groups. The second polymer derivative may be a polymer (e.g., a hyaluronic acid) modified with one or more thiol groups.

A mass ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

A molar ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

A volume ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

In some cases, the first polymer derivative may have a first DM (DM1), the second polymer derivative may have a second DM (DM2), and a ratio between the first DM (DM1) and the second DM (DM2) may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10), such as from about 3:1 to about 1:3, or from about 2:1 to about 1:2, such as about 1:1.

In some embodiments, the first polymer derivative and the second polymer derivative in the composition may have a mass ratio as defined in the present disclosure, a molar ratio as defined in the present disclosure, a volume ratio as defined in the present disclosure, and/or a DM ratio as defined in the present disclosure.

According to any aspect of the present disclosure, the first modification and the second modification may be each independently selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof. The first modification and the second modification may be different from each other.

Accordingly, the first polymer derivative (or the polymers in the first polymer population) may be a polymer of the present disclosure modified with one or more vinylsulfone groups (or with a molecule comprising one or more vinylsulfone groups), and the second polymer derivative (or the polymers in the second polymer population) may be a polymer of the present disclosure modified with one or more thiol groups (or with a molecule comprising one or more thiol groups). The first polymer derivative (or the polymers in the first polymer population) may be able to react with the second polymer derivative (or the polymers in the second polymer population) to form the hydrogel.

In another example, the first polymer derivative (or the polymers in the first polymer population) may be a polymer of the present disclosure modified with one or more thiol groups (or with a molecule comprising one or more thiol groups), and the second polymer derivative (or the polymers in the second polymer population) may be a polymer of the present disclosure modified with one or more vinylsulfone groups (or with a molecule comprising one or more vinylsulfone groups). The first polymer derivative (or the polymers in the first polymer population) may be able to react with the second polymer derivative (or the polymers in the second polymer population) to form the hydrogel.

In some embodiments, the polymer is a hyaluronic acid, the first polymer population (or the first polymer derivative) comprises hyaluronic acids modified with one or more vinylsulfone groups. The second polymer population (or the second polymer derivative) comprises hyaluronic acids modified with one or more thiol groups. Polymers of the first polymer population (or the first polymer derivatives) are able to react with polymers of the second polymer population (or the second polymer derivatives) to form the hydrogel.

In another example, the polymer is a hyaluronic acid, the first polymer population (or the first polymer derivative)

comprises hyaluronic acids modified with one or more thiol groups. The second polymer population (or the second polymer derivative) comprises hyaluronic acids modified with one or more vinylsulfone groups. Polymers of the first polymer population (or the first polymer derivatives) are able to react with polymers of the second polymer population (or the second polymer derivatives) to form the hydrogel.

According to any aspect of the present disclosure, the polymer in the composition may have an average molecular weight from about 100,000 to about 5,000,000 dalton, e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton.

The polymer of the present disclosure may comprise one or more modifications (also referred to as polymer derivatives in the present disclosure), and they may have an average degree of modification of about 3% to about 50%, e.g., about 4% to about 50%, about 5% to about 50%, about 6% to about 50%, about 7% to about 50%, about 8% to about 50%, about 9% to about 50%, about 10% to about 50%, about 11% to about 50%, about 12% to about 50%, about 13% to about 50%, about 14% to about 50%, about 15% to about 50%, about 16% to about 50%, about 17% to about 50%, about 18% to about 50%, about 19% to about 50%, about 20% to about 50%, about 21% to about 50%, about 22% to about 50%, about 23% to about 50%, about 24% to about 50%, about 25% to about 50%, about 26% to about 50%, about 27% to about 50%, about 28% to about 50%, about 29% to about 50%, about 30% to about 50%, about 31% to about 50%, about 32% to about 50%, about 33% to about 50%, about 34% to about 50%, about 35% to about 50%, about 36% to about 50%, about 37% to about 50%, about 38% to about 50%, about 39% to about 50%, about 40% to about 50%, or about 40% to about 50%.

For example, the composition may comprise at least a first polymer population comprising the polymer modified with a first modification (i.e., the first polymer derivative) and a second polymer population comprising the polymer modified with a second modification (i.e., the second polymer derivative). The total concentration $C_T$ of the polymers (e.g., hydrogel forming polymers) in the composition may be at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). The first polymer derivative may have an average DM of about 3% to about 50% (e.g., about 5% to about 35%, about 8% to about 35%, about 10% to about 35%, about 12% to about 35%, about 15% to about 35%, about 20% to about 35%, about 25% to about 35%, or about 30% to about 35%), with an average molecular weight of about 100,000 to about 5,000,000 dalton (e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton). The second polymer derivative may have an average DM of about 3% to about 50% (e.g., about 5% to about 35%, about 8% to about 35%, about 10% to about 35%, about 12% to about 35%, about 15% to about 35%, about 20% to about 35%, about 25% to about 35%, or about 30% to about 35%), with an average molecular weight of about 100,000 to about 5,000,000 dalton (e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton). A ratio (e.g., a mass ratio, a volume ratio, a molar ratio, and/or a DM ratio) between the first polymer derivate and the second polymer derivate in the composition may be from about 10:1 to about 1:10 (such as from about 3:1 to about 1:3, or from about 2:1 to about 1:2, such as about 1:1). The first polymer derivative may be capable of reacting with the second polymer derivative to form the hydrogel. In addition, the first polymer derivative may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in said composition. The second polymer derivative may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in said composition.

The concentration C of the first polymer derivative may be about 0.8 to about 5 times (e.g., about 0.8 to about 4.5 times, about 0.8-about 4.0 times, about 0.8-about 3.5 times, about 0.8-about 3.0 times, about 0.8-about 2.5 times, about 0.8-about 2.0 times, about 0.8 to about 1.5 times, or about 1.0 to about 1.2 times) of a concentration C*, the C*=1/([η]), and the [η] is the intrinsic viscosity of the first polymer derivative.

The concentration C of the second polymer derivative may be about 0.8 to about 5 times (e.g., about 0.8 to about 4.5 times, about 0.8-about 4.0 times, about 0.8-about 3.5 times, about 0.8-about 3.0 times, about 0.8-about 2.5 times, about 0.8-about 2.0 times, about 0.8 to about 1.5 times, or about 1.0 to about 1.2 times) of a concentration C*, the C*=1/([η]), and the [η] is the intrinsic viscosity of the second polymer derivative.

In some cases, the composition does not comprise any crosslinker different from the polymers (e.g., the first polymer derivative, or the second polymer derivate) in the composition.

In some embodiments, the composition does not comprise any small molecule crosslinker or any PEG based crosslinker.

In a specific example, the first polymer derivative is a hyaluronic acid modified with one or more vinylsulfone groups (e.g., HA-VS), and the second polymer derivative is a hyaluronic acid modified with one or more thiol groups (e.g., HA-SH).

In some cases, the composition or the polymer solution of the present disclosure may comprise a crosslinker (e.g., a crosslinker different from the polymers in the composition).

The crosslinker may be a small molecule crosslinker, a macromolecule crosslinker, or a combination thereof. In some embodiments, the crosslinker is a small molecule crosslinker, and it may comprise molecules containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and/or combinations thereof.

In some embodiments, the crosslinker is a macromolecule crosslinker, and it may comprise macromolecules containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and/or combinations thereof.

For example, the composition may comprise a polymer of the present disclosure modified with one or more thiol groups (e.g., a polymer derivative of the present disclosure) and a crosslinker, the crosslinker may be a vinylsulfone containing molecule, for example, the crosslinker may be selected from the group consisting of divinyl sulfone, Bis(vinylsulfonyl)methane, PEG-VS and 4 or 8 arm-PEGVS.

In another example, the composition may comprise a polymer of the present disclosure modified with one or more vinylsulfone groups (e.g., a polymer derivative of the present disclosure) and a crosslinker, the crosslinker may be a thiol containing molecule, for example, the crosslinker may be selected from the group consisting of dithiothreitol, di-cysteine, PEG-dithiol, and 4 or 8 arm-PEG thiol.

The hydrogel of the present disclosure may enhance material's resistance to drainage on surfaces (e.g., a mucosal surface). The hydrogel of the present disclosure may have excellent fluidic property similar to that of an aqueous solution. The hydrogel of the present disclosure may have an excellent property of resisting to drainage.

Thus, the present disclosure also relates to the following embodiments:
1. A composition comprising a polymer capable of forming a hydrogel, wherein said polymer has a concentration C that is about 0.8-about 5 times of a concentration C*, wherein C*=1/([η]), and [η] is an intrinsic viscosity of said polymer.
2. The composition according to embodiment 1, wherein said polymer has a concentration C that is about 0.8-about 1.5 times of the concentration C*.
3. The composition according to embodiment 1, wherein said polymer has a concentration C that is about 1.0-about 1.2 times of the concentration C*.
4. The composition according to embodiment 1, wherein said polymer has a concentration C that is about 1.8-about 2.0 times of the concentration C*.
5. The composition according to any of the preceding embodiments, wherein said polymer has a [η] that is at least 3 dL/g.
6. The composition according to any of the preceding embodiments, wherein said polymer has a [η] that is at least 5 dL/g.
7. The composition according to any of the preceding embodiments, wherein said polymer has a [η] that is at least 20 dL/g.
8. The composition according to any of the preceding embodiments, wherein said polymer is hydrophilic and/or water soluble.
9. The composition according to any of the preceding embodiments, wherein said polymer is selected from the group consisting of a polysaccharide, a poly(acrylic acid), a poly(hydroxyethylmethacrylate), an elastin, a collagen, and combinations thereof.
10. The composition according to any of the preceding embodiments, wherein said polymer is selected from the group consisting of a poly (acrylic acid), a poly(hydroxyethylmethacrylate), and combinations thereof.
11. The composition according to any of the preceding embodiments, wherein said polymer is selected from the group consisting of a hyaluronic acid, a guar gum, a starch, a chitosan, a chondroitin sulfate, an alginate, a carboxymethylcellulose, and combinations thereof.
12. The composition according to any of the preceding embodiments, wherein said polymer is selected from the group consisting of a hyaluronic acid, a guar gum, an alginate, a carboxymethylcellulose, and combinations thereof.
13. The composition according to any of the preceding embodiments, wherein said polymer is a hyaluronic acid.
14. The composition according to any of the preceding embodiments, wherein said polymer is modified with one or more modifications selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and combinations thereof.
15. The composition according to any of the preceding embodiments, wherein said polymer is modified with one or more modifications selected from the group consisting of a maleimide, a vinylsulfone, a N-hydroxysuccinimide, an aldehyde, a mercaptonicotinamide, a quinone, a thiol, an amine, and combinations thereof.
16. The composition according to any of the preceding embodiments, wherein said polymer comprises at least a first polymer population comprising said polymer modified with a first modification and a second polymer population comprising said polymer modified with a second modification, wherein said first modification is different from said second modification, and wherein polymers of said first polymer population react with polymers of said second polymer population to form the hydrogel.

17. The composition according to embodiment 16, wherein a ratio between the polymers comprised in said first polymer population and the polymers comprised in said second polymer population is from about 10:1 to about 1:10.

18. The composition according to embodiment 17, wherein a ratio between the polymers comprised in said first polymer population and the polymers comprised in said second polymer population is from about 3:1 to about 1:3.

19. The composition according to embodiment 18, wherein a ratio between the polymers comprised in said first polymer population and the polymers comprised in said second polymer population is from about 2:1 to about 1:2.

20. The composition according to any of embodiments 16-19, wherein said first modification and said second modification are independently selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and combinations thereof.

21. The composition according to any of embodiments 16-19, wherein said first modification and said second modification are independently selected from the group consisting of a maleimide, a vinylsulfone, a N-hydroxysuccinimide, an aldehyde, a mercaptonicotinamide, a quinone, a thiol, an amine, and combinations thereof.

22. The composition according to embodiment 21, wherein said polymer is a hyaluronic acid, said first polymer population comprises hyaluronic acids modified with one or more vinylsulfone groups, said second polymer population comprises hyaluronic acids modified with one or more thiol groups, and wherein polymers of said first polymer population react with polymers of said second polymer population to form the hydrogel.

23. The composition according to any of the preceding embodiments, wherein said polymer has an average molecular weight from about 100,000 to about 5,000,000 dalton.

24. The composition according to any of the preceding embodiments, wherein said polymer has an average molecular weight from about 120,000 to about 5,000,000 dalton.

25. The composition according to any of the preceding embodiments, wherein said polymer has an average molecular weight from about 670,000 to about 5,000,000 dalton.

26. The composition according to any of the preceding embodiments, wherein said polymer has an average molecular weight from about 2,600,000 to about 5,000,000 dalton.

27. The composition according to any of the preceding embodiments, wherein said polymer has an average molecular weight from about 3,600,000 to about 5,000,000 dalton.

28. The composition according to any of the preceding embodiments, wherein said polymer has an average molecular weight from about 2,600,000 to about 3,600,000 dalton.

29. The composition according to any of the preceding embodiments, wherein said polymer has an average molecular weight from about 670,000 to about 2,600,000 dalton.

30. The composition according to any of the preceding embodiments, wherein said polymer comprises polymers with modifications, and said polymer has an average degree of modification of about 3% to about 50%.

31. The composition according to any of the preceding embodiments, wherein said polymer comprises polymers with modifications, and said polymer has an average degree of modification of about 8% to about 35%.

32. The composition according to any of the preceding embodiments, wherein said polymer comprises polymers with modifications, and said polymer has an average degree of modification of about 15% to about 35%.

33. The composition according to any of the preceding embodiments, wherein said polymer comprises polymers with modifications, and said polymer has an average degree of modification of about 15% to about 30%.

34. The composition according to any of the preceding embodiments, wherein said polymer has a concentration C of about 0.1 mg/ml to about 5 mg/ml.

35. The composition according to any of the preceding embodiments, wherein said polymer has a concentration C of about 0.3 mg/ml to about 0.6 mg/ml.

36. The composition according to any of the preceding embodiments, further comprising a cross-linker, wherein the cross-linker is a small molecule cross-linker, a macromolecule cross-linker, or a combination thereof.

37. The composition according to embodiment 36, wherein the cross-linker is a small molecule cross-linker comprising molecules containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and/or combinations thereof.

38. The composition according to embodiment 36, wherein the cross-linker is a macromolecule cross-linker comprising macromolecules containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and/or combinations thereof.

39. The composition according to embodiment 36, wherein said polymer is modified with one or more vinylsulfone groups and said cross-linker is a thiol containing molecule.

40. The composition according to embodiment 39, wherein said cross-linker is selected from the group consisting of dithiothreitol, di-cysteine, PEG-dithiol, and 4 or 8 arm-PEG thiol.

41. The composition according to embodiment 36, wherein said polymer is modified with one or more thiol groups and said cross-linker is a vinylsulfone containing molecule.

42. The composition according to embodiment 41, wherein said cross-linker is selected from the group consisting of divinyl sulfone, Bis(vinylsulfonyl)methane, PEG-VS and 4 or 8 arm-PEGVS.
43. The composition according to any of embodiments 1-35, wherein said composition does not comprise a crosslinker different from said polymer.
44. The composition according to any of the preceding embodiments, wherein said composition comprises a buffer.
45. The composition according to embodiment 44, wherein said buffer comprises a phosphate buffer.
46. The composition according to any of the preceding embodiments, wherein said composition has a pH of about 3.5 to about 9.0.
47. The composition according to any of the preceding embodiments, wherein said composition has a pH of about 7.0 to about 7.8.
48. The composition according to any of the preceding embodiments, wherein said composition has a pH of about 7.4.
49. A hydrogel formed by a composition according to any of embodiments 1-48.
50. The hydrogel according to embodiment 49, wherein said hydrogel is biocompatible.
51. The hydrogel according to any of embodiments 49-50, wherein said hydrogel has a storage modulus that is no more than about 10.0 Pa, as measured by a dynamic oscillatory shear test.
52. The hydrogel according to any of embodiments 49-51, wherein said hydrogel has a storage modulus that is no more than about 5.0 Pa, as measured by a dynamic oscillatory shear test.
53. The hydrogel according to any of embodiments 49-52, wherein said hydrogel has a storage modulus that is no more than about 1.0 Pa, as measured by a dynamic oscillatory shear test.
54. The hydrogel according to any of embodiments 49-53, wherein said hydrogel has a storage modulus that is no more than about 0.6 Pa, as measured by a dynamic oscillatory shear test.
55. The hydrogel according to any of embodiments 49-54, wherein said hydrogel has a loss modulus that is no more than about 100% of the storage modulus as measured by a dynamic oscillatory shear test.
56. The hydrogel according to any of embodiments 49-55, wherein said hydrogel has a loss modulus that is no more than about 50% of the storage modulus as measured by a dynamic oscillatory shear test.
57. The hydrogel according to any of embodiments 49-56, wherein said hydrogel has a loss modulus that is no more than about 25% of the storage modulus as measured by a dynamic oscillatory shear test.
58. The hydrogel according to any of embodiments 49-57, wherein said hydrogel has a complex viscosity that is no more than about 0.2 Pa·s as measured by a dynamic oscillatory shear test at a frequency of more than about 100 rad/s.
59. The hydrogel according to any of embodiments 49-58, wherein said hydrogel has a complex viscosity that is no more than about 0.1 Pa·s as measured by a dynamic oscillatory shear test at a frequency of more than about 100 rad/s.
60. The hydrogel according to any of embodiments 49-59, wherein said hydrogel has a complex viscosity that is no more than about 0.05 Pa·s as measured by a dynamic oscillatory shear test at a frequency of more than about 100 rad/s.
61. A method for generating a hydrogel, comprising: providing a composition comprising a polymer according to any of embodiments 1-48; and subjecting said composition to conditions enabling crosslinking of said polymer to form the hydrogel.
62. The method according to embodiment 61, wherein said subjecting comprises incubating said polymer solution at about 30° C. to about 45° C.
63. The method according to embodiment 62, wherein said subjecting comprises incubating said polymer solution at about 37° C.
64. The method according to any of embodiments 61-63, wherein the hydrogel generated is according to any one of embodiments 49-60.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Measurement of HA Samples 1.1. Measurement of [η]

[η] can be measured directly using capillary viscometers. For example, three HA samples, namely, sample A, sample B and sample C, were measured by a Ubbelohde viscometer. These HA samples were purchased form Bloomage Freda Biopharm Co. Ltd. (Shandong, China). The polymers were measured by the supplier according to the European Pharmacopeia. Table 1 shows the intrinsic viscosity ([η]) of sample A, sample B and sample C measured by a Ubbelohde viscometer.

TABLE 1

| Intrinsic viscosity ([η]) measured by a Ubbelohde viscometer | | | | |
|---|---|---|---|---|
| | | Sample A | Sample B | Sample C |
| Ubbelohde viscometer | [η] | 39.2 dL/g | 14 dL/g | 3.7 dL/g |

1.2 Estimation of the Molecular Weight of the Polymers

The molecular weight (MW) of a polymer was calculated from the intrinsic viscosity value measured by Ubbelohde viscometer, using the Mark-Houwink-Sakurada equation:

$$[\eta] = K_M (MW)^a$$

wherein $K_M$ and a (Mark-Houwink-Sakurada exponent) are constants for a given polymer-solvent pair.

The MW of the sample A, B and C was calculated to be 2.6 MDa, 670 KDa and 120 KDa for the sample A, B and C accordingly.

Example 2

Preparation of Polymer Derivatives 2.1 The Preparation of HA-VS

Hyaluronic acids (HA) were modified with pedant VS as described by Yu and Chau (*Biomacromolecules* 2015, 16 (1), 56-65). Briefly, HA was dissolved in deionized water (DI water). The concentration was from 1 mg/ml to 40 mg/ml depending on molecular weight (MW) of HA. For high MW HA (e.g. MW>500 kDa), the concentration was lower (e.g. from 1 mg/ml to 5 mg/ml), for low MW HA (e.g., MW<500 kDa), the concentration was higher (e.g. 5 mg/ml to 40 mg/ml).

After complete dissolution, 5M NaOH was added drop wise to the polymer solution to a final concentration at 0.1M. Divinylsulfone (DVS) was added instantly with vigorous mixing. Alternatively, DVS was first dissolved in DI water at 1 mg (DVS)/8 ml (water) and added instantly into the vigorously mixing polymers. The molar ratio between DVS and hydroxyl groups (OH) of HA was at least 1.25:1. For low concentration of HA, the molar ratio was 6:1 or higher. The reaction time was chosen depending on the target degree of modification (DM). For a given reaction time, the degree of modification was also depending on the concentration of both HA and DVS, the temperature and the final NaOH concentration.

For the HA sample C (the molecular weight of 120 kDa), the HA concentration was 20 mg/ml, and the molar ratio between DVS and OH of HA was 1.5:1; for the HA sample B (the molecular weight of 670 kDa), the HA concentration was 10 mg/ml, and the molar ratio between DVS and OH of HA was about 3:1; and for the HA sample A (the molecular weight of 2.6 MDa), the HA concentration was 2.5 mg/ml, and the molar ratio between DVS and OH of HA was about 6:1.

The reaction was stopped by adding 6M HCl. The polymers were purified by membrane separation using dialysis bag or tangential flow filtration against DI water (about pH 5.5) or acidic DI water of about pH 4 adjusted by HCl. The purified polymer was stored as a solution at 4° C. For measuring the degree of modification (DM), HA-VS was freeze dried and measured by $^1$HNMR.

2.2 The Preparation of HA-SH

Hyaluronic acids (HA) were modified with pedant SH group as described by Yu and Chau (*Biomacromolecules* 2015, 16 (1), 56-65). Briefly, HA was first modified to HA-VS (as described in Example 2.1). The HA-VS solution was purged with $N_2$ for at least 20 minutes. Dithiothreitol (DTT) of 10× molar excess to VS group or the amount needed to make a 0.05M DTT solution (depending on which DTT concentration is higher) was dissolved in water (pH about 5.5) at about 400 mg/ml and purged with $N_2$ for at least 5 minutes and added to the HA-VS solution. The pH of the HA-VS/DTT solution was around 4 and the system was continued to be purged with $N_2$. Afterwards, 0.5M phosphate buffer (PB) of 1/10 the volume of HA-VS was purged with $N_2$ for at least 5 minutes and added to the HA-VS/DTT solution. The reaction was allowed for at least 25 minutes. The reaction was stopped by adding 1M HCl to reduce the pH to 3.5-4.5. The polymers were purified by membrane separation using dialysis bag or tangential flow filtration against DI water, or DI water of pH 4 adjusted by HCl. The purified polymer was stored as a solution at 4° C. The degree of modification (DM) was determined by $^1$HNMR and Ellmans' assay for HA-SH.

Figure 2:
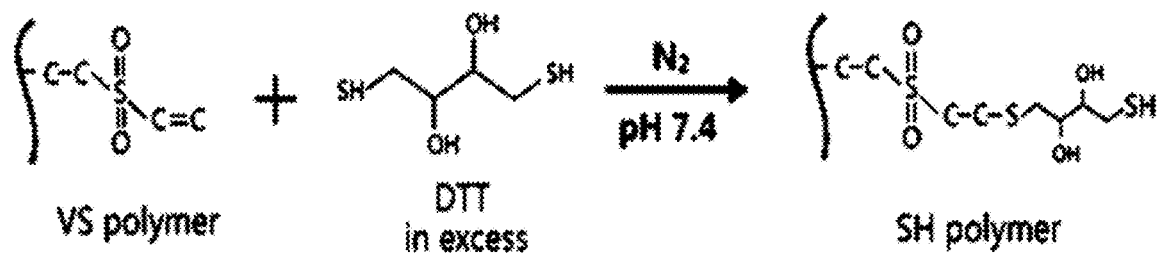
FIG. 2 illustrates the synthesis of HA-SH polymer.

Synthesis of vinylsulfonated hyaluronic acid (HA-VS) was shown in FIG. 1. And thiolated hyaluronic acid (HA-SH) was synthesized according to FIG. 2.

Example 3

Hydrogel Formation 3.1. Formation of HA-VS/HA-SH Based Polymer-Polymer Type Hydrogel The concentration of HA-VS and HA-SH was first determined. The polymer solution of known volume was freeze dried and the dry weight of polymer was measured. The dry polymer was at least 4 mg to ensure accurate measurement. Alternatively, the polymer concentration was measured by CTAB assay as described previously (Oueslati et al., CTAB turbidimetric method for assaying hyaluronic acid in complex environments and under cross-linked form, Carbohydrate Polymers, 2014). HA-VS and HA-SH of known concentration was then adjusted to pH 7.4 by the addition of 0.5M PB. The final concentration of PB was about 0.02M to 0.05M. The osmolality was then adjusted using 25% NaCl. The polymers were then mixed at various target volume ratio and mass ratio, and adjusted to the target concentration by adding phosphate buffered saline (PBS).

Figure 3:
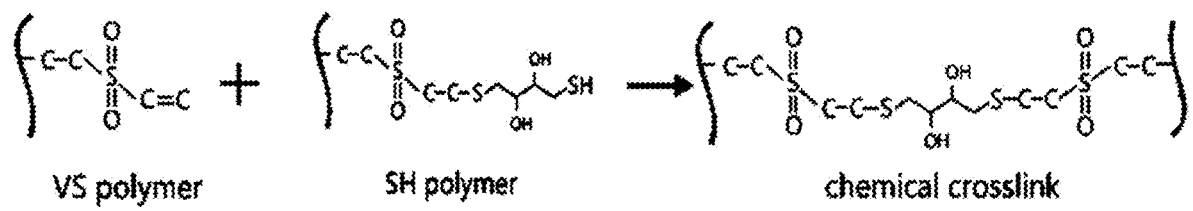
FIG. 3 illustrates the synthesis of the hydrogel of the present disclosure.

The polymers were incubated at 37° C. for at least 10 hours for hydrogel formation. The hydrogel formation reaction is demonstrated in FIG. 3.

For HA polymers with an average molecular weight of about 2.6 MDa, with an intrinsic viscosity [η] of about 39.2 dL/g (as measured by a Ubbelohde viscometer), the concentration of the HA polymers (including both the HA-SH and the HA-VS) for forming the HA-VS/HA-SH based polymer-polymer type hydrogel of the present disclosure can be as low as about 0.4 mg/ml (i.e., water content in the hydrogel is more than about 99.96%).

In the present disclosure, the samples A1, A2, A3, A4, A5, A6, A7, A8 and A9 of HA-SH/HA-VS polymer-polymer type hydrogel were prepared based on HA polymers of Sample A in Example 1.1 (with an average molecular weight of about 2.6 MDa and an intrinsic viscosity [η] of about 39.2 dL/g). For samples A1, A2, A3 and A4, the $C_T$ of the hydrogel forming polymers (e.g., the total concentration of the HA-VS and the HA-SH) was about 1.2 mg/ml, 0.8 mg/ml, 0.5 mg/ml and 0.27 mg/ml, respectively, and the DM of the HA-VS and HA-SH was about 10%, respectively, the molar and mass ratio between HA-VS and HA-SH was 1:1. For Sample A5, the hydrogel was formed by mixing the HA-VS and HA-SH at 1:1 DM ratio and 1:1 mass ratio, the total concentration $C_T$ of the hydrogel forming polymers in the composition was about 0.5 mg/ml, and the DM of the HA-VS and HA-SH was about 20%, respectively. For sample A6, the hydrogel was formed by mixing the HA-VS (with a DM of 8%) and HA-SH (with a DM of 8%) at 1:1 DM ratio and 1:1 mass ratio, the total concentration $C_T$ of the hydrogel forming polymers in the composition was about 0.45 mg/ml. For sample A7, the hydrogel was formed by mixing the HA-VS (with a DM of 30%) and HA-SH (with a DM of 30%) at 1:1 DM ratio and 1:1 mass ratio, the total concentration $C_T$ of the hydrogel forming polymers in the composition was about 0.4 mg/ml. For sample A8, the hydrogel was formed by mixing the HA-VS (with about 10% DM and 0.6 mg/ml) and the HA-SH (with about 5% DM and 0.3 mg/ml) and the $C_T$ is about 0.9 mg/ml. For sample A9, the hydrogel was formed by mixing the HA-VS (with 15% DM and 0.6 mg/ml) and the HA-SH (with 10% DM and 0.3 mg/ml), and the $C_T$ is about 0.9 mg/ml.

The samples B1 and B2 of HA-SH/HA-VS polymer-polymer type hydrogel were prepared based on HA polymers of Sample B in Example 1.1 (with an average molecular weight of about 670 kDa and an intrinsic viscosity [η] of about 14 dL/g). For samples B1 and B2, the $C_T$ of the HA polymers (including both the HA-SH and the HA-VS) was about 1.8 mg/ml and 1.08 mg/ml, respectively. The DM of HA-SH and HA-VS was 30%, and the molar and mass ratio between HA-SH and HA-VS was 1:1.

The sample C1 of HA-SH/HA-VS polymer-polymer type hydrogel was prepared based on HA polymers of Sample C in Example 1.1 (with an average molecular weight of about 120 kDa and an intrinsic viscosity [η] of about 3.7 dL/g). For the sample C1, the $C_T$ of the HA polymers (including both the HA-SH and the HA-VS) was about 3.96 mg/ml. The DM of HA-SH and HA-VS was 30%, and the molar and mass ratio between HA-SH and HA-VS was 1:1.

3.2 Formation of HA-SH Based Polymer-Polymer Type Hydrogel

Sample A of HA polymer (with a weight average molecular weight of about 2.6 MDa, and an intrinsic viscosity [η] of about 39.2 dL/g) was used. HA-SH was prepared according to Example 2.2. The HA-SH was adjusted to pH 7.4 by the addition of 0.5M PB. The final concentration of PB was about 0.02M to 0.05M. The DM of the polymer was about 10%. The polymer was then adjusted to the target concentration by adding phosphate buffered saline (PBS). Sample F of HA-SH polymer-polymer type hydrogel was prepared with a $C_T$ of about 1.7 mg/ml.

The polymers were incubated at 37° C. for at least 10 hours for hydrogel formation.

3.3. Formation of Polymer-Small Molecular Crosslinker Type Hydrogel

DTT was mixed with HA-VS (the HA-VS was prepared based on HA polymer of Sample A) at 3:1 molar ratio (DTT:VS). A hydrogel was formed after 30 minutes. The hydrogel was dialyzed against double deionized water for 2 days and collected. The HA-VS has a weight average molecular weight of about 1.9 MDa, an intrinsic viscosity [η] of about 24.5 dL/g and a total polymer (e.g., hydrogel forming polymer) concentration $C_T$ of about 3.8 mg/ml. The DM of the HA-VS was 20%. The obtained HA-SH/DTT hydrogel was named as Sample H of HA-SH/DTT hydrogel.

Example 4

Hydrogel Characterization 4.1 Modulus of the Prepared Hydrogel Samples (1) Preparation of Hydrogel Samples for Measurement The hydrogel forming polymers were mixed as described in Example 3, and then the mixed polymers were spread evenly on a mold of 50 mm(D)×1 mm(H). The mold was adhered to a metal plate by covering the plate with parafilm. The mold with polymers was placed in a humidified chamber, and hydrogel was allowed to form. For hydrogel formation, the polymers were kept at 37° C. for 24 hours. After hydrogel formation (i.e., the HA-VS/HA-SH based polymer-polymer type hydrogel), the whole parafilm-mold-gel assembly was detached from the metal plate and mounted on a 50 mm plate fixture. The mold was then removed, leaving the parafilm and the formed hydrogel on the fixture. Parafilm was then firmly wrapped around a bottom plate. The setup was loaded to a DMA machine (ARES Rheometer, TA Instruments, New Castle, DE), and the mechanical properties were measured with a parallel plate of 50 mm diameter.

Alternatively, the hydrogel forming polymers were mixed as described in Example 3 and then incubating at 37° C. for at least 10 hours (e.g., 24 hours unless specified) in a centrifuge tube. The hydrogel formed (i.e., the HA-VS/HA-SH based polymer-polymer type hydrogel) was then loaded onto the lower plate or lower bucket of a cone-plate, double-gap or co-centric cylinder fixture, and the mechanical properties were measured by an Anton Paar rheometer.

(2) The Modulus of HA-VS/HA-SH Based Polymer-Polymer Hydrogels

Three samples of HA polymers (i.e., Sample A, B and C described in Example 1.1 and 1.2 above) were modified according to Example 2.1 and 2.2, and the modified polymers were used to form a hydrogel of the present disclosure according to Example 3.1, the hydrogels formed were measured according to Example 4.1. To determine whether the polymers formed a hydrogel instead of remaining as a polymer solution, DMA measurement and/or direct observation (to see whether or not the samples flow like water and cannot be mounted to a DMA machine) was used. For DMA measurement, a higher G' value comparing to G'' value (e.g., G''/G'<1) at the linear viscoelastic region (LVR) region was used as an indication for hydrogel formation.

The results are summarized in Table 2 below. The mechanical properties were measured at the LVR region of the gel. The inventors surprisingly found that when the intrinsic viscosity [η] of the hydrogel forming polymers in a composition is relatively high (e.g., at least about 3 dL/g, as measured by a Ubbelohde viscometer), and the total concentration $C_T$ of the hydrogel forming polymers (e.g., the HA-VS and the HA-SH) in the composition was relatively low (e.g., lower than about 5 mg/ml such as 1.2, 0.8, 0.5, 1.8, 1.08 and 3.96 mg/ml, respectively), a very soft hydrogel may be formed, as shown by the G' and G'' of the hydrogels. The G' and the G'' were no more than 10.0 Pa, indicating the formation of hydrogel.

TABLE 2

Gel formation of different hydrogel formulations

| MW (Da) | Concentration (mg/ml) | G' (Pa) | G'' (Pa) | hydrogel formation |
|---|---|---|---|---|
| 2.6M (sample A) | 1.2 (sample A1) | 3.8 ± 0.09 | 0.13 ± 0.01 | yes |
| | 0.8 (sample A2) | 0.87 ± 0.03 | 0.07 ± 0.01 | yes |
| | 0.5 (sample A3) | 0.12 ± 0.01 | 0.03 ± 0.01 | yes |
| | 0.27 (sample A4) | 0.028 ± 0.02 | 0.036 ± 0.03 | no |
| 670k (sample B) | 1.8 (sample B1) | 17.44 ± 0.49 | 5.33 ± 0.33 | yes |
| | 1.08 (sample B2) | 4.70 ± 0.40 | 1.55 ± 0.12 | yes |
| 120k (sample C) | 3.96 (sample C1) | 40.52 ± 0.39 | 9.03 ± 1.98 | yes |

Figure 4:
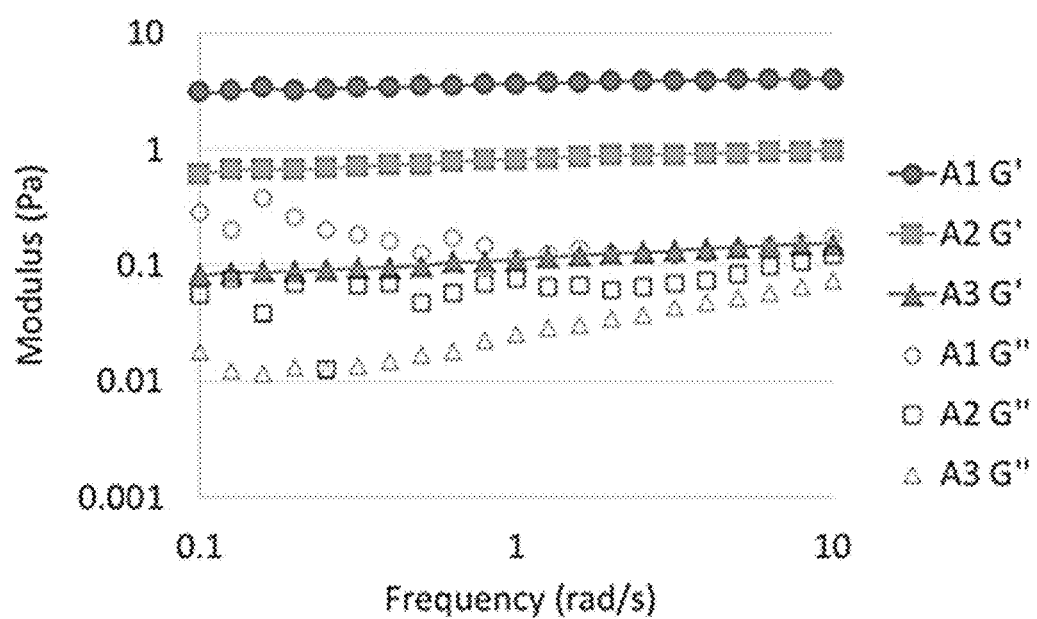
FIG. 4 illustrates the modulus of the hydrogel of the present disclosure.

FIG. 4 shows the modulus (using frequency sweep test) of the sample A1, A2 and A3 of HA-VS/HA-SH based polymer-polymer type hydrogel prepared according to Example 3.1, the modulus of the hydrogel was measured by a rheometer Anton Paar MCR502 with co-centric double gap fixture. The strain was 1% for all tests.

Figure 5:
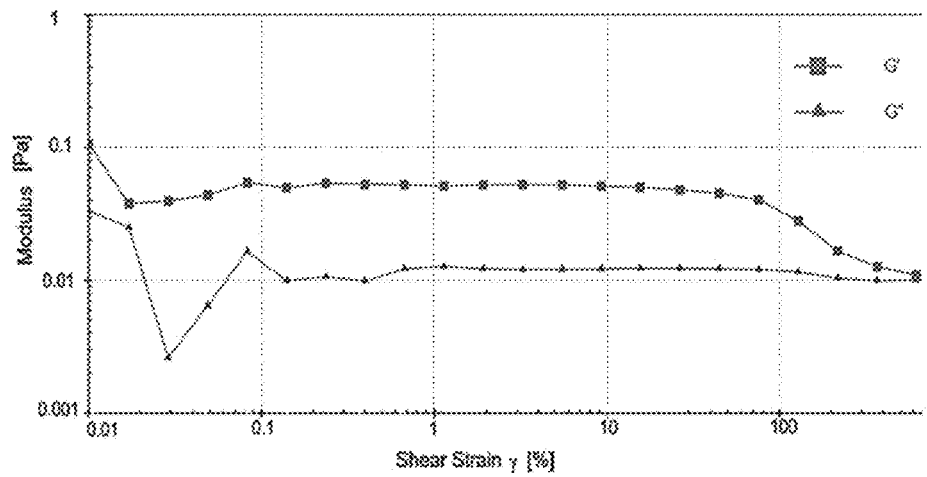
FIG. 5 illustrates the modulus of the hydrogel of the present disclosure.

FIG. 5 shows the modulus (using strain sweep test) of the sample A8 of HA-VS/HA-SH based polymer-polymer type hydrogel prepared according to Example 3.1, using Anton Paar MCR502 with co-centric double gap fixture. The frequency was 1 rad/s. The $C_T$ of sample A8 of HA-VS/HA-SH based polymer-polymer type hydrogel was 0.9 mg/ml, which was lower than 5 mg/ml. Both the G' and G'' were no more than 10.0 Pa. And G" was less than G', indicating the formation of hydrogel.

FIG. 6A and FIG. 6B show the modulus and complex viscosity (using strain and frequency sweep test) of the sample A9 of HA-VS/HA-SH based polymer-polymer type hydrogel prepared according to Example 3.1, using Anton Paar MCR302 with 50 mm cone-plate fixture. The frequency was 5 rad/s for strain sweep test and the strain was 5% for frequency sweep test. The $C_T$ of sample A9 of HA-VS/HA-SH based polymer-polymer type hydrogel was 0.9 mg/ml, which was lower than 5 mg/ml. Both the G' and G" were no more than 10.0 Pa. And G" was less than G', indicating the formation of hydrogel.

(3) The Modulus of HA-SH Polymer-Polymer Hydrogel

Figure 7:
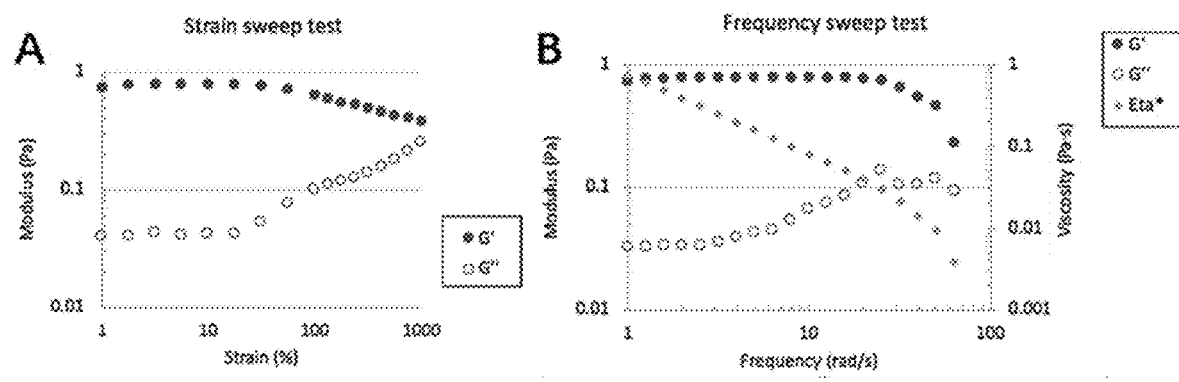
FIGS. 7A and 7B illustrates the strain sweep test and frequency sweep test of the hydrogel of the present disclosure.

FIGS. 7A and 7B illustrate the strain sweep test and frequency sweep test of Sample F of HA-SH polymer-polymer type hydrogel of 10% DM prepared according to Example 3.2. In FIG. 7, G', G" and Eta* refer to storage modulus, loss modulus and complex viscosity, respectively. The hydrogel was measured using an Anton Paar MCR 302 rheometer with 50 mm cone-plate fixture. The strain sweep test was measured at 5 rad/s and the frequency sweep test was measured at 5% strain. The $C_T$ of sample F of HA-SH polymer-polymer type hydrogel was 1.7 mg/ml, which was lower than 5 mg/ml. Both the G' and G" were no more than 10.0 Pa. And G" was less than G', indicating the formation of hydrogel.

(4) The Modulus of HA-SH Polymer-Small Molecular Crosslinker Type Hydrogel

FIGS. 8A and 8B illustrate the strain sweep test and frequency sweep test of Sample H of HA-SH/DTT hydrogel which was prepared according to Example 3.3. The strain sweep test was measured at 1 rad/s and the frequency sweep test was measured at 5% strain, in which G', G" and Eta* refer to storage modulus, loss modulus and complex viscosity, respectively. The $C_T$ of sample H of HA-SH/DTT hydrogel was about 3.8 mg/ml, which was lower than 5 mg/ml. Both the G' and G" were no more than 10.0 Pa. And G" was less than G', indicating the formation of hydrogel.

The results above shows that for all the tested hydrogels, the storage modulus (G') is higher than its corresponding lost modulus (G"), and the value of G' is relatively constant in a dynamic oscillatory shear test at a frequency of from about 0.1 rad/s to about 10 rad/s, indicating that the material is indeed a gel (i.e., a very soft solid-like crosslinked network), instead of a viscous solution.

4.2 The Yield Strain of the Hydrogel

The yield strain can be evaluated by strain sweep tests (FIGS. 5~8). For example, the results in FIG. 5 and FIG. 7 show that the hydrogels have a relatively high yield strain (about 30%) with a low yield stress (about 0.1 to about 1 Pa).

4.3 The Recovery From Yield of the Hydrogel By Strain Sweep Test

With the low yield point, one may have expected that the hydrogel of the present disclosure is mechanically unstable. Surprisingly, the mechanical properties of the hydrogel of the present disclosure can be similar before and after destruction. In this example, sample A3 of HA-VS/HA-SH based polymer-polymer type hydrogel prepared according to Example 3.1 was used to test the recovery from yield of the hydrogel by strain sweep test.

The sample A3 of HA-VS/HA-SH based polymer-polymer type hydrogel was loaded to a co-centric double gap fixture on Anton Paar MCR502. Before and after performing a strain sweep test from 0 to 5000% to destroy the hydrogel, time sweep tests (1% strain and 1 rad/s) were performed to evaluate the modulus of the hydrogel. The hydrogel was equilibrated for about 5 min before each measurement. The G' and G" before destruction was about 0.11 Pa and 0.02 Pa, after destruction was 0.11 Pa and 0.05 Pa. The result shows that the modulus was almost identical before and after destruction.

4.4 The Complex Viscosity of Hydrogels

Figure 6:
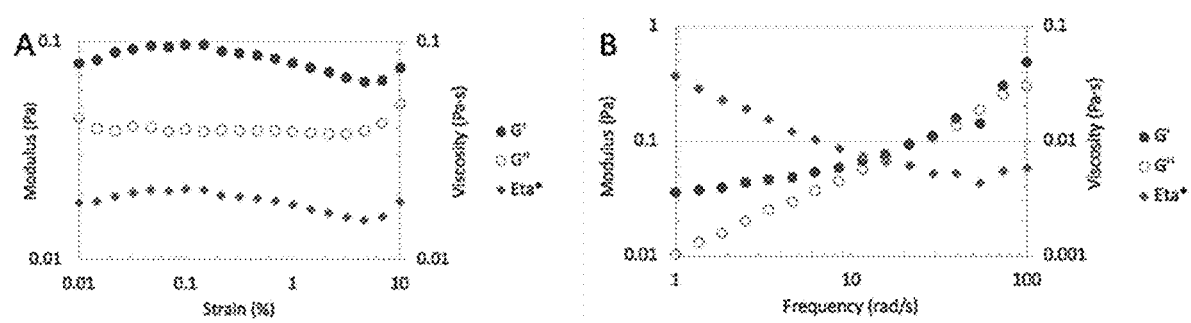
FIGS. 6A and 6B illustrates the modulus and complex viscosity of the hydrogel of the present disclosure.
Figure 8:
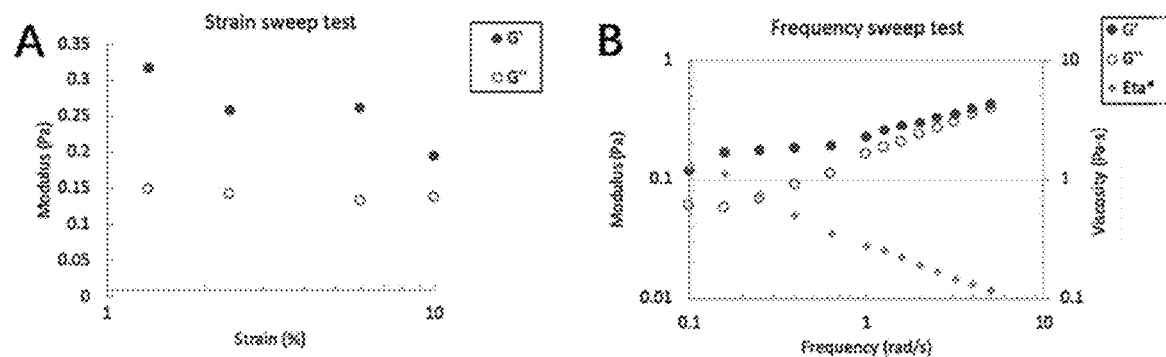
FIGS. 8A and 8B illustrates the strain sweep test and frequency sweep test of the hydrogel of the present disclosure.

The frequency sweep test of hydrogels, as shown in FIGS. 6~8, indicate that the complex viscosity of the hydrogel becomes small at a relatively slow frequency (e.g. Eta*<0.01 Pa at frequency about 10-100 rad/s). These results indicate that the hydrogel of the present disclosure will be easy to be spreaded across a surface with the help of a small force. In addition, viscosity of the hydrogel according to the present disclosure increases exponentially towards low shear rate, indicating that it is stable at rest.

Example 5

Preparation of the Fluorescent Dye Conjugation 5.1. Tagging Fluorescent Probe to the Polymer The hydrogel of the present disclosure was made fluorescent by tagging a fluorescent dye on the polymer of the present disclosure. A thiol modified fluorescein was used as a dye example. The dye was made by reacting aminofluorescein with N-Acetyl-S-trityl-L-cysteine in DMF, catalyzed by HOBT/HBTU. The product was precipitated in ether for 3 times and dried in vacuum. The dried product was deprotected with a mixture of TFA:$H_2O$:TIPS (18:1:1) for 1 hour. The final product was precipitated in ether and dried in vacuum and stored at 4° C. The progress of the reaction was determined by mass spectrometry.

5.2. The Fluorescent Dye Conjugation

In one example, HA-VS was adjusted to pH 8.8 by adding 1.5M Tris buffer of pH 8.8 to a final buffer concentration of 0.15M. The solution was purged with $N_2$ for at least 30 minutes. Afterwards, a vinylsulfone reactive dye, either made according to Example 5.1 or purchased from GL Biochem (Shanghai) Ltd. (a cysteine-lysine di-peptide with the amino group of the lysine side chain conjugated with a fluorescein and the amino end group capped by an amide, or AC-Cys-Lys(FAM), was dissolved in Tris buffer and added to the polymer to react for 12 hours. The molar ratio between the dye and VS group can be up to 1:1 for low DM (e.g. DM=8%) polymer, as the conjugation efficiency is not high, and the reaction will not cover all VS groups. Ideally, at least 80% of VS groups should not be covered by the dye after reaction. The polymer was then dialyzed against DI water adjusted to about pH 4 using HCl. The storage condition for the purified fluorescent-labeled polymer was the same as for HA-VS. Then, the fluorescent-labeled HA-VS was mixed with HA-SH and hydrogels were allowed to form the hydrogel (as described in Example 3).

Figure 9:
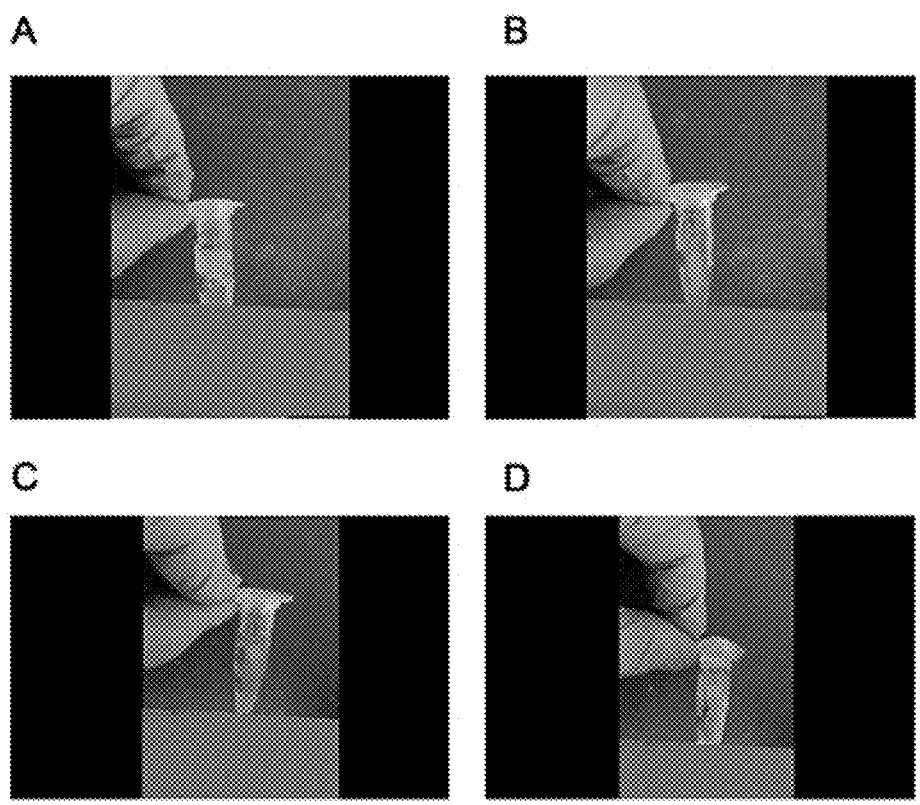
FIGS. 9A-9D provide an example illustrating the mechanical properties of the hydrogel.

The formed hydrogel (for example, sample A6, which was formed by mixing the HA-VS (with a DM of 8%) and HA-SH (with a DM of 8%) at 1:1 DM ratio and 1:1 mass ratio, the total concentration $C_T$ of the hydrogel forming polymers in the composition was about 0.45 mg/ml), was observed to be resistant to water dilution due to its special mechanical properties (e.g., the properties discussed in Example 4 above). As shown in FIGS. 9A~9D, the hydrogel of the present disclosure was able to move freely in water without dissolution (FIG. 9A and FIG. 9B), and after 24 hours, the hydrogel was not dissolved and could still move freely in water without dissolution (FIG. 9C and FIG. 9D).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition comprising two or more hydrogel forming polymers wherein, before they are added to the composition, at least two hydrogel forming polymers have an intrinsic viscosity [η] of at least 3 dL/g in said composition as measured by a Ubbelohde viscometer, and wherein the concentration $C_T$ of each of said two or more hydrogel forming polymers in said composition before they are added to the composition and prior to combining and mixing them to form a hydrogel is about 0.3 mg/ml to about 5 mg/ml, wherein said two or more hydrogel forming polymers comprises a first polymer derivative and a second polymer derivative, wherein said first wherein said first polymer derivative comprises a first modification and said second polymer derivative comprises a second modification, wherein said first modification is different from said second modification, and said first polymer derivative is capable of reacting with said second polymer derivative to form a hydrogel, wherein said first modification and said second modification are each independently selected from the group consisting of an acrylate, a maleimide, a vinylsulfone, a N-hydroxysuccinimide, an aldehyde, a ketone, a carbodiimide, a carbonate, an iodoacetyl, a mercaponicotinamide, a quinone, a thiol, an amine, and any combinations thereof, wherein said hydrogel that is formed by combining said two or more hydrogel forming polymers has at least one of the following:

1) A storage modulus G' that is no more than about 10.0 Pa, as measured in a dynamic oscillatory shear test;

2) A complex viscosity that is no more than about 0.2 Pa·s as measured in a dynamic oscillatory shear test at a frequency of more than about 100 rad/s; and 3) A yield strain of at least about 10%, as measured in a dynamic oscillatory strain sweep test; wherein said two or more hydrogel forming polymers is selected from the group consisting of a hyaluronic acid, a derivative thereof, and any combinations thereof.

2. The composition according to claim 1, wherein at least some of said two or more hydrogel forming polymers are comprised in said composition in a hydrogel formed.

3. The composition according to claim 1, wherein said two or more hydrogel forming polymers are hydrophilic and/or water soluble.

4. The composition according to claim 1, having at least one of the following:

1) A mass ratio between said first polymer derivative and said second polymer derivative in said composition is from about 10:1 to about 1:10, 2) A molar ratio between said first polymer derivative and said second polymer derivative in said composition is from about 10:1 to about 1:10, 3) A volume ratio between said first polymer derivative and said second polymer derivative in said composition is from about 10:1 to about 1:10, and 4) said first polymer derivative has a first degree of modification (DM), said second polymer derivative has a second DM, and a ratio between said first DM and said second DM is from about 10:1 to about 1:10.

5. The composition according to claim 1, wherein said two or more hydrogel forming polymers are hyaluronic acid derivatives, said first polymer derivative is a hyaluronic acid modified with one or more vinylsulfone groups, said second polymer derivative is a hyaluronic acid modified with one or more thiol groups, and wherein said first polymer derivative is capable of reacting with said second polymer derivative to form said hydrogel.

6. The composition according to claim 1, wherein said composition does not comprise any crosslinker different from said two or more hydrogel forming polymers.

7. A hydrogel formed by the composition according to claim 1.

8. The hydrogel according to claim 7, wherein said hydrogel has a loss modulus G" that is no more than about 100% of its storage modulus G', as measured in a dynamic oscillatory shear test.

9. A method for generating a hydrogel, comprising:
a) providing the composition according to claim 1; and
b) mixing polymer of said first polymer derivative and said second polymer derivative at a ratio of about 1:1, the concentration (C) of said polymers is about 0.3-0.5 mg/mL.

* * * * *